United States Patent [19]
Lessard et al.

[11] Patent Number: 5,603,160
[45] Date of Patent: Feb. 18, 1997

[54] METHOD FOR MAKING AN EXTRACTION CARTRIDGE

[75] Inventors: Denis Lessard, Vaudreuil; John H. Burrows, Pierrefonds, both of Canada

[73] Assignee: Phoenix International Life Sciences Inc., Montreal, Canada

[21] Appl. No.: 419,403

[22] Filed: Apr. 10, 1995

Related U.S. Application Data

[62] Division of Ser. No. 235,713, Apr. 29, 1994.

[51] Int. Cl.$^6$ .................................................. B23P 15/16
[52] U.S. Cl. ...................... 29/896.62; 210/266; 422/70
[58] Field of Search ............................. 29/163.8; 422/69, 422/70; 210/266, 282; 73/61.52, 61.53

[56] References Cited

U.S. PATENT DOCUMENTS 5,084,168  1/1992  Woog ...................................... 210/266

FOREIGN PATENT DOCUMENTS 2034946  7/1991  Canada .
0446970  9/1991  European Pat. Off. .

OTHER PUBLICATIONS

Partial European Search Report filed on Jun. 29, 1995.
Journal of Pharmaceutical 7 Biomedical Analysis, vol. 11, No. 4/5, 1993, Permagon Press, GB, pp. 277–284, M. Casas et al., "Solid-Phase extraction of 1,4–benzodiazepines from Biological Fluids".
Journal of Pharmaceutical 7 Biomedical Analysis, vol. 10, No. 1992, Pergamon Press, GB, pp. 937–942, Hubert P. Chiap et al. "Determination of Varapamil and Noverapamil in Human Plasma by Liquid–Chromatography—parison Between a Liquid–Liquid–Extraction Procedure and an Automated Liquid Solid Extraction Method for Sample Preparation".
Therapeutic Drug Monitoring, vol. 13, No. 2, 1991, ISSN 0163–4356, pp. 157–165, Verbesselt R., "High-Performance Liquid-Chromatographic Determination of 12 Antiarrhythmic drugs in Plasma Using Solid-Phase Column Extraction".

*Primary Examiner*—P. W. Echols
*Attorney, Agent, or Firm*—Greenblum & Bernstein P.L.C.

[57] ABSTRACT

An extraction cartridge, for extracting a component from a composition, contains a packing composition including a buffer composition, diatomaceous earth and absorbent. The cartridge is made by heating each component to assure it is free from contaminants. The diatomaceous earth is sifted to obtain a particular particle size. The cartridge also includes frits and filters for holding the packing composition within the cartridge. All of the components of the cartridge are selected or processed to assure that no contaminants are leached into the sample being extracted. A processing system automatically processes a plurality of cartridges. The processing system, which is capable of continuous operation, includes a platform, a rack for holding the cartridges, sample vials and extraction tubes. A walking beam conveyor system moves the rack along the platform and a system of robotic arms automatically transfers the sample to be extracted from the sample vial to the extraction cartridge and adds a predetermined amount of solvent into the extraction cartridge. The extraction process includes adding a sample into the extraction cartridge, waiting a predetermined time, adding a predetermined amount of solvent and collecting the solvent in a collection tube. The processing system can be controlled by a computer system including a dual microprocessor.

1 Claim, 27 Drawing Sheets

METHOD FOR MAKING AN EXTRACTION CARTRIDGE

This application is a Division of application Ser. No. 08/235,713, filed Apr. 29, 1994, pending.

BACKGROUND OF THE INVENTION

1. Field of the Invention

The present invention relates to cartridges for extracting a substance from a composition and a process for making the cartridges. Further, the present invention relates to a method for extracting a substance from a composition. More specifically, the present invention relates to a method for extracting a drug from a biological sample so that the drug is extracted with good recovery and without extraneous components that would cause interferences during analysis. Still further, this invention relates to an automatic processing apparatus for extracting substances from a composition.

2. Discussion of Background Information

One of the main areas of activity of pharmaceutical companies, contract research laboratories and medical laboratories is the determination of drug levels in samples of human and animal complex biological fluids such as blood, plasma, serum and urine. The drugs are usually present in extremely low concentrations and the most sensitive detection devices are required for their quantification. It is therefore necessary that the drug be separated from all other materials present in the complex biological fluids since the other materials could cause interference during analysis. This separation step is generally referred to as the sample preparation step.

The need to extract only the drug from the other components of the complex biological fluid is becoming increasingly important with the development of increasingly sensitive analytical techniques like gas chromotography/electron capture detector (GC/ECD), gas chromatography/nitrogen phosphorus detector (GC/NPD), gas chromotography/mass spectroscopy (GC/MS) and liquid chromotography/mass spectroscopy (LC/MS). These methods allow drug detection at the low nanogram/ml and even picogram/ml levels.

Extraction of drugs from biological fluids is presently achieved by one of three procedures: liquid-liquid extraction, solid phase extraction and liquid-liquid extraction on a solid phase support, called Thin-Film Liquid-Liquid Extraction. Each of these procedures will be briefly described.

(a) Liquid-Liquid Extraction

Liquid-liquid extraction involves shaking the biological fluid with a water immiscible organic solvent, at a pH that favors the equilibrium distribution of the drug preferentially into the organic solvent. The organic solvent containing the extracted drug is then separated from the aqueous phase, and either evaporated prior to injection into a chromatograph, or subjected to additional cleanup procedures (e.g., extraction into an aqueous phase and back extraction into an organic phase) followed by chromatography.

Liquid-liquid extraction has several disadvantages, such as being very labor intensive, subject to variation in extraction efficiency, and prone to operator errors. Also, emulsion formation can prevent a clean separation of the organic solvent from the aqueous phase, and variable amounts of contaminants are carried through the extraction process, with their presence usually requiring a chromatography time of 5–60 minutes.

(b) Solid Phase Extraction

Solid phase extraction involves use of a short plastic column containing a sorbent, designed to differentially adsorb the drug and contaminants. The column is usually preconditioned with a solvent mixture, the biological fluid is then applied, the drug and other substances are adsorbed or absorbed on the column, water soluble contaminants are washed off, and finally the drug, along with contaminants, is washed off the column with an organic solvent. As with liquid-liquid extraction, the extract can then be evaporated and chromatographed, or further processed before chromatography.

Solid phase extraction has several advantages over liquid-liquid extraction in that it is often somewhat less labor intensive than liquid-liquid extraction, and provides extracts of apparently comparable cleanliness when using high pressure liquid chromatography (HPLC) as the analytical technique. However, solid phase extraction has several disadvantages. Specifically, use of gas chromatography (GC) with solid phase extracts reveals that while the columns used in the extraction remove many contaminants from the biological fluid, they also introduce new contaminants from the column themselves, and this has almost invariably prevented the use of solid phase extraction for sensitive GC procedures. Additionally, evaporation of eluates from many of these columns leaves behind a powdery residue, derived from the column, that renders GC analysis impossible and shortens HPLC column life.

c) Thin-Film Liquid-Liquid Extraction

Thin-film liquid-liquid extraction involves adding biological fluid to a cartridge containing an essentially inert support, usually diatomaceous earth. An organic solvent is then washed through the cartridge to extract the drug from the film of the biological fluid spread over the inert support. This technique is not commonly used with biological fluids, because the extracts are usually too contaminated with endogenous materials to allow subsequent chromatography, and the percentage extracted is often low.

It is generally recognized that thin-film liquid-liquid extraction is disadvantageous in that the proportion of drug recovered from a thin-film liquid-liquid extraction of a biological fluid is inversely related to the selectivity of the extraction. Thus, virtually complete extraction of a drug can be obtained with a polar solvent, such as diethyl ether, but the extract is often too contaminated to be useful. Conversely, if a highly non-polar solvent, such as pentans, is used for extraction, the extracts tend to be substantially cleaner, but only between about 0–50% of the drug is extracted and the amount extracted is more variable.

Accordingly, while greater selectivity is achieved with relatively non-polar solvents, sensitivity and precision are sacrificed. The sensitivity of the extraction can be improved by extracting the biological fluid with several aliquots of the organic solvent, but precision tends not to be improved, or it can even be degraded due to the errors incurred in multiple operations.

One method for overcoming the disadvantages of thin-film liquid-liquid extractions has been to develop conditions where multiple extractions of the biological fluid with several aliquots of a relatively non-polar solvent could be performed with minimal variability. This should be achievable using commercially available diatomaceous earth cartridges. However, while these cartridges appear to be useful for a few drugs, they cannot be generally applied for three reasons:

a) Most drugs are either basic, acidic or amphoteric, and these drugs tend not to be extracted with commercially available cartridges unless the pH of the biological, fluid is first adjusted. At high sensitivity levels, the drug tends to be lost through adhesion to glass surfaces once the pH is changed;

b) The non-polar solvent required to obtain relatively clean extracts also dissolves fatty materials from the biological fluid, which often interfere with subsequent chromatography; and c) Extracts from these cartridges suffer from moderate to severe contamination with materials derived from the biological fluid and the cartridge itself.

Despite the many attempts to automate solid phase and liquid-liquid extraction techniques, there is no equipment that allows the rapid, continuous processing of a large number of samples. Most systems handle one sample at throughputs of 3–5 samples per hour. Others can only perform a specific task but not the whole separation procedure. It would therefore be highly desirable to develop a fully automatic, continuous system for the whole extraction process.

Canadian Laid Open Patent Application 2,034,946, which is hereby incorporated by reference in its entirety, discloses an inert solid phase extraction column. The column includes an elongate barrel made from glass or any other material that does not dissolve or leach contaminants. The column contains a packing material, such as silica, that has been cleaned by soaking, serial extraction or fluidized bed flow using a variety of solvents. The packing material is held within the barrel by a pair of meshes positioned above and below the packing material. A stop in the barrel prevents the bottom mesh from moving outside the barrel. A retaining ring disposed on the top mesh maintains pressure to keep the packing material confined to a predetermined portion of the glass barrel.

SUMMARY OF THE INVENTION

An object of the present invention is to provide an extraction technique based on an extraction cartridge that produces isolated drug samples that can be analyzed without any further purification steps. Furthermore, it is an object of the present invention to provide an extraction method that can be readily automated to reduce the considerable cost of manual labor due to the time consuming, repetitive nature of presently available procedures.

Another object of the present invention is to provide a fully automated system that will extract drugs from most biological fluids with greatly increased specificity using the principle of repetitive thin-film liquid-liquid extraction.

Another object of the present invention is to provide a multilayer extraction cartridge filled with materials on which the biological sample is absorbed and/or adsorbed and through which a water immiscible organic solvent or solvent mixture is passed in repetitive aliquots to selectively elute the drug.

Still another object of the present invention is to provide a process for manufacturing a multilayer extraction cartridge.

Still another object of the present invention is to provide automated equipment that allows the continuous processing of biological samples with the organic solvents including a fully automatic liquid handling and dispensing system that employs a walking beam to continuously move samples and cartridges through the extractor.

It is accordingly an object of the present invention to provide an extraction cartridge, comprising a barrel comprising an upper opening for feeding of a fluid to be extracted and a lower opening for removal of treated fluid; and a multilayer packing composition within the barrel, the multilayer packing composition comprising a buffer layer comprising a buffer material for adjusting pH of the fluid to be extracted; and a partitioning layer positioned below the buffer layer, the partitioning layer comprising a material for spreading fluid into a thin-film.

The barrel can comprise an inert material, preferably selected from the group consisting of glass, ceramic and metal, and more preferably the inert material is glass.

The buffer material can comprise particles, preferably having a particle size of about 100 to 1000 microns. Moreover, the buffer layer can comprise buffer material and an inert material, preferably particles of inert material, preferably having a particle size of about 200 to 3000 microns. Preferably, the inert material is at least one member selected from the group consisting of crystalline silica, glass beads, metal balls, ceramic beads, crushed rock, washed sand and diatomaceous earth, more preferably crystalline silica.

Moreover, the buffer material can comprise particles of buffer material, preferably having a particle size of about 100 to 1000 microns.

Further, the buffer layer can comprise buffer material coated on particles of inert material, such as particles having a particle size of about 600 to 850 microns. These insert particles are preferably selected from the group consisting of crystalline silica and diatomaceous earth, more preferably diatomaceous earth.

In each of the embodiments of the buffer layer according to the present invention, the buffer material can comprise at least one member selected from the group consisting of oxalic acid, tartaric acid, citric acid, succinic acid, ammonium dihydrogen phosphate, sodium dihydrogen phosphate, potassium dihydrogen phosphate, aluminum sulphate, ammonium oxalate, diammonium hydrogen phosphate, sodium bicarbonate, potassium bicarbonate, disodium hydrogen phosphate, dipotassium hydrogen phosphate, borax, tris(hydroxymethyl)methylamine, sodium carbonate, potassium carbonate, trisodium phosphate and tripotassium phosphate. Further, the buffer layer can comprise about 5–50 wt % buffer material and about 95–50 wt % inert material, more preferably about 10–30 wt % buffer material and about 90–70 wt % inert material, and even more preferably the buffer layer comprises about 20 wt % buffer material and about 80 wt % inert material.

The material for partitioning a fluid into a thin-film can comprise a particulate material, such as a particulate material having a particle size of about 200 to about 3000 microns. The particulate material can comprise at least one member selected from the group consisting of silica gels, fibrous cellulose, fibrous glass and diatomaceous earth, and is preferably diatomaceous earth.

The multilayer composition can additionally comprise at least one additional layer, preferably a plurality of layers. These additional layers can comprise at least one component selected from the group consisting of a component for removing moisture, a component for removing extraneous materials, and a component for derivatizing a drug into a more readily analyzable form.

The component for removing moisture can comprise at least one member selected from the group consisting of anhydrous sodium sulphate, anhydrous magnesium perchlorate, anhydrous calcium sulphate, copper sulphate and alumina, preferably anhydrous sodium sulphate.

The component for removing extraneous materials can comprise at least one member selected from the group consisting of alumina, Florisil®, and silica gel. The component for derivatizing a drug into a more readily analyzable form can comprise reactive alkyl halides such as pentafluorobenzyl bromide.

The cartridge can include a filter positioned below the multilayer composition for retaining the multilayer packing composition within the barrel, preferably made from at least one material selected from the group consisting of stainless steel mesh, glass mesh, porous polyolefins, porous polytetrafluoroethylene, glass fiber mat and cellulose, more preferably cellulose.

The cartridge can include a filter positioned above the multilayer composition, for maintaining the multilayer packing composition within the barrel, preferably comprising at least one material selected from the group consisting of stainless steel mesh, cellulosic material and glass fiber mat, more preferably stainless steel mesh.

A further embodiment of the present invention is a method for making an extraction cartridge comprising heating an inert support at a temperature of about 500° C. for about 3 hours, mixing the heated inert support with a buffer; heating diatomaceous earth at a temperature of about 500° C. for about 3 hours; heating an adsorbent at a temperature of about 500° C. for about 3 hours; positioning a frit at the bottom of a cartridge; adding the heated adsorbent to the cartridge; adding the heated diatomaceous earth to the cartridge; adding the mixture of heated inert support and buffer to the cartridge; and positioning a filter in the cartridge.

A still further embodiment of the present invention is an extraction cartridge comprising a barrel comprising an upper opening for feeding of a fluid to be extracted and a lower opening for removal of treated fluid; and a multilayer packing composition within the barrel, the multilayer packing composition comprising a buffer layer for adjusting pH including about 95–50 wt % buffer material and about 5–50 wt % inert support; a partitioning layer comprising a particulate material for spreading a fluid into a thin film; a filter positioned above the multilayer packing composition for retaining the multilayer packing composition within the barrel; and a filter positioned below the multilayer packing composition for retaining the multilayer composition within the barrel.

An additional embodiment of the present invention is a method of extracting a component from a fluid comprising adding a fluid containing a component to be extracted to an extraction cartridge comprising a barrel comprising an upper opening for feeding of a fluid to be extracted and a lower opening for removal of treated fluid; and a multilayer packing composition within the barrel, the multilayer packing composition comprising a buffer layer comprising a buffer material for adjusting pH of the fluid to be extracted; and a partitioning layer positioned below the buffer layer, the partitioning layer comprising a material for spreading fluid into a thin-film; waiting a period of time for the fluid to spread out into a thin film over the partitioning layer; adding a first organic solvent to the cartridge to extract the component from the fluid into the first organic solvent; and collecting the first organic solvent containing the component.

The method for extraction can also include evaporating the collected solvent and adding a second organic solvent to redissolve the extracted component. The fluid being extracted can be a biological fluid. Preferably the biological fluid is selected from the group consisting of human plasma, human serum, human urine, animal plasma, animal serum and animal urine.

The first organic solvent can be at least one member selected from the group consisting of pentane, hexane, carbon tetrachloride, cyclohexane, iso-propylether, chlorobutane, chloroform, diethylether, toluene and ethyl acetate. The second organic solvent is a polar solvent. Preferably, the polar solvent is at least one member selected from the group consisting of methanol, ethyl acetate and ethanol.

The method of extracting can also include waiting a period of time for the component being extracted to partition between the fluid and the first solvent; and repeating the steps of adding a first organic solvent to the cartridge to extract the component from the fluid into the first organic solvent; and collecting the first organic solvent containing the component.

A still further embodiment of the present invention is an automatic processing system for extraction of components from a fluid, comprising a main processing platform; indexing means for raising, lowering and incrementally advancing a rack along the main processing platform; and means for automatically transferring fluids at predetermined positions along the main processing platform. The indexing means can be at least one walking beam positioned at the main processing platform.

The processing system can be structured and arranged for continuous handling of racks, such as by including extensions for the feeding and removal of racks, or can be structured and arranged to permit handling of racks in a batch mode of operation.

The main processing platform includes a working surface, and a walking beam can include at least one elongated member, with the elongated member being mounted so as to be movably positionable between a lower position wherein an upper surface of the elongated member is below the working surface, and an upper position wherein the upper surface of the walking beam is above the working surface.

The at least one elongated member moves from the lower position to the upper position and returns to the lower position, the at least one elongated member is capable of incrementally moving a rack along the main processing platform. The at least one elongated member can be two elongated members. The at least one elongated member can be eccentrically mounted on at least two pulleys, and each of the at least two pulleys is mounted on a rotatable shaft.

The indexing means further comprises a motor for rotating the rotatable shaft, and means for controlling activation of the motor to enable control of a degree of rotation of the rotatable shaft. The means for controlling activation of the motor comprise elements to stop rotation of the at least two pulleys after one revolution to obtain precise incremental movement. The indexing means further includes at least one locking pin movable from a first position above the working surface to a second position below the working surface as the elongated member moves from the lower position to the upper position, and movable from the second position below the working surface to the first position above the working surface as the elongated member moves from the upper position to the lower position. The at least one locking pin extends to a maximum height of about 0.75 inches above the working surface in the first position.

The processing system further includes a rotatable cam associated with each the at least one locking pin, the at least one locking pin including a lower end contacting the cam. The cam is preferably a pear-shaped cam.

The at least one elongated member moves from the lower position to the upper position and returns to the lower position, the at least one elongated member is capable of incrementally moving a rack along the location, and the at least one elongated member is eccentrically mounted on at least two pulleys, and each of the at least two pulleys and the cam is mounted on a rotatable shaft.

The upper surface of the at least one elongated member includes elements for engaging a lower surface of a rack. The elements for engaging can be protrusions on the upper surface of the at least one elongated member or elements for increasing frictional engagement along the upper surface of the at least one elongated member.

The working surface of the processing system includes means defining openings corresponding to each of the at least one elongated member and the at least one locking pin to permit passage therethrough. The working surface also can include guide rails.

The means for automatically transferring fluids at predetermined positions includes at least one robotic arm movable along a width, length and height of the location. The at least one robotic arms can be two independently movable robotic arms, wherein each of the two robotic arms includes at least one probe for transferring fluids. The processing system further includes at least one syringe pump connected by at least one valve with the at least one probe. The at least one probe comprises a plurality of probes, preferably four probes.

The means for controlling activation of the motor to enable control of a degree of rotation of the rotatable shaft comprise at least one proximity sensor. Preferably, the proximity sensor is a photosensor.

The processing system further includes a wash rack. The wash rack includes at least one wash station and at least one internal standard tube. The processing system can include an input extension platform for feeding a rack onto the main processing platform. The input extension platform includes at least one proximity sensor and a conveyor belt. The processing system can include output extension platform for receiving a rack from the main processing platform. The output extension platform comprises at least one proximity sensor and a conveyor belt.

The processing system can include a computer system for controlling the operation of the indexing means, and the means for automatically transferring fluids at predetermined positions. The computer system includes a master system and a slave sub-system. The master system controls operation of the means for automatically transferring fluids. The slave sub-system controls operation of the indexing means. The processing system can include a keyboard with a display, and the slave-subsystem controls the keyboard with a display, The automatic processing system further includes at least one rack, the at least one rack including a lower rack including a back portion, a front portion, and a bottom surface, the back portion including openings for receiving collection vessels, and the front portion including a plurality of openings for receiving sample vessels; an upper rack positioned above the back portion of the lower rack, the upper rack including a plurality of openings for receiving cartridges; and the bottom surface includes at least one element for locking the rack along the main processing platform. The at least one element comprises a plurality of equally spaced openings along the bottom surface. The bottom surface of can be a roughened surface.

BRIEF DESCRIPTION OF THE DRAWINGS

Embodiments of the present invention are shown in the accompanying drawings, in which like reference numerals represent similar parts throughout the several views of the drawings, wherein.

DETAILED DESCRIPTION OF THE PREFERRED EMBODIMENTS

Figure 1B:
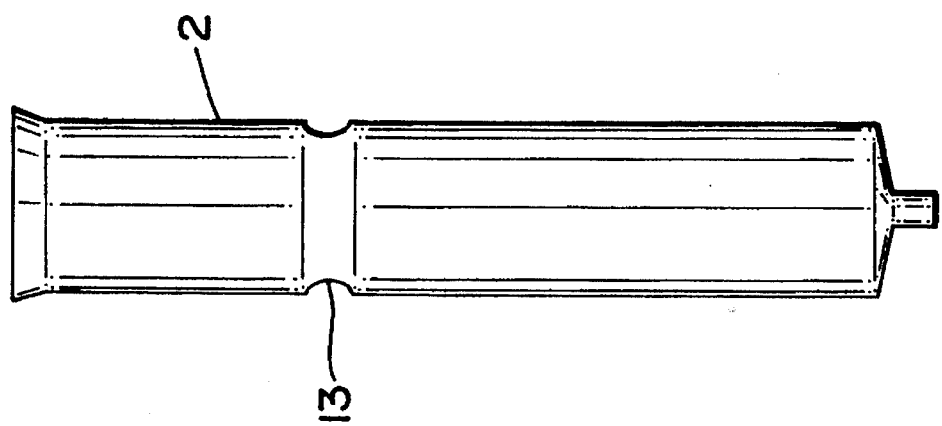
FIG. 1b is a cross-sectional view of another embodiment of the cartridge of the present invention.
Figure 1A:
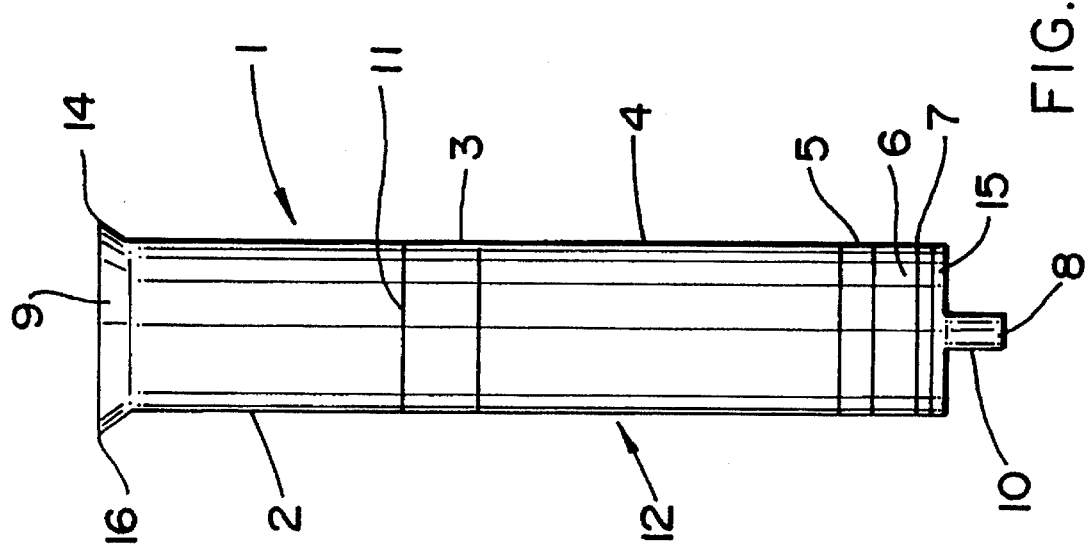
FIG. 1a is a cross-sectional view of the cartridge according to the present invention.

As shown in FIG. 1a, the cartridge 1 according to the present invention includes an elongated barrel 2 having an inlet end 9 and an outlet end 8. Optionally, the cartridge can include a flare 14 at the inlet end 9 and a bottom portion 15 extended by a nipple 10 at the outlet end 8. The elongated barrel 2 can be made from any material that does not dissolve or leach contaminants into the composition being extracted.

The cartridge 1 contains a multilayered packing composition 12 positioned between the inlet end 9 and the outlet end 8. The multilayered packing composition comprises a number of layers to effect a spreading out of the sample, to control pH and to permit the selective flow of the eluate through the packing composition. To accomplish these objectives the multilayer composition includes at least a buffer layer 3 and a partition layer 4 for spreading the sample being extracted into a thin film on a solid support. Further, the multilayer packing composition can comprise any number of additional layers, such as a layer to remove moisture, a layer to remove other extraneous materials, and a layer including materials that derivatize the drug being extracted so that it is in a more readily analyzable form. Further, the additional layers can include components to provide a combination of functions. For example, one additional layer can have any number of combined function, such as combined moisture removing and derivatizing functions.

As illustrated in FIG. 1a, in a preferred form of the invention, the uppermost layer 3, positioned toward the inlet of the barrel, disperses the sample evenly over the top of the cartridge and adjusts the pH. The layer 4, beneath the layer 3 includes a composition for spreading the sample being extracted into a thin film. Further, in the illustrated embodiment two layers 5 and 6 are shown below the partition layer 4. Either of these layers can have the function of removing traces of water from the organic solvent or mixture of organic solvents, selectively absorb and/or adsorb non-polar materials, other than the drug, that would otherwise contaminate the extract, as well as derivatize the drug being extracted into a more readily analyzable form. For example, layer 5 can be anhydrous sodium sulphate and layer 6 can be basic, acid or neutral alumina to provide specific interactions with drugs or contaminants. Other possible selective absorbers are Florisil®, such as Florisil® A and Florisil® PR, and silica gels. An example of a derivatization agent is pentafluorobenzyl bromide which reacts preferentially with phenolic compounds at specific pH.

The packing composition 12 is held within the elongated barrel 2 by filters or frits 7, 11, which will be more specifically described later, placed below and above the packing composition 12, respectively. The filter or frits 7, 11 are constructed of materials that do not introduce contaminants and prevent the packing composition from being washed out of the barrel 2, but do not impede liquid flow.

The cartridge 1 according to the present invention can have any dimension depending upon the extraction being performed and the packing composition used. Specifically, the cartridge can be from about 10 and 200 mm in height, measured from the top 16 to the bottom portion 15, with an outer diameter, from about 5 and 40 mm and an inner diameter from about 3 and 36 mm. Preferably, the cartridge can be from about 30 and 120 mm in height with an outer diameter, from about 5 and 25 mm and an inner diameter from about 3 and 23 mm. Even more preferably, the cartridge can be about 67.0 mm in height with an outer diameter, of about 14.5 mm and an inner diameter of about 11.7 mm.

As shown in .FIG. 1b, an alternative embodiment of the cartridge according to the present invention includes a constriction 13 that reduces the diameter of the barrel 2. The constriction can be placed at any position sufficient to accommodate the packing composition in the barrel. The constriction 13 can be at a distance from about 1 mm to 100 mm from the top of the cartridge, preferably, from about 1 mm to 40 mm from the top of the cartridge, and even more preferably, about 22 mm from the top of the cartridge. The constriction 13 can reduce the diameter of the cartridge from about 0.5 mm to 10 mm, preferably, from about 0.5 mm to 5 mm, and even more preferably, by about 1.0 mm.

In this embodiment, the top filter is positioned immediately under the constriction. The filter is pushed past the constriction 13 causing slight compression of the packing. On release, the filter will push up against the constriction. Thus, the packing is immobilized, preventing mixing of the layers during handling and transporting.

As has been described above, the cartridge according to the present invention includes a barrel, a buffer layer, a partition layer, and optionally at least one additional layer such as a drying agent/absorber layer and frits or filters. Each of the components of the cartridge will be described in detail below.

Barrel

Any material that does not leach contaminants into the extract can be used to construct the barrel. For example, inert materials such as glass, metals including aluminum, nickel, stainless steel, titanium, or ceramic can be used to make the barrel. Preferably, the material of construction of the barrel is glass. An even more preferred barrel is a glass, syringe-type barrel cartridge with a molded, one piece construction available from Burdick and Jackson (Custom SPE Cartridge Cat. No. 79.99GB supplied by Canlab, 2390 Argentia Rd., Mississauga, Ont.). Prior to being filled with the packing material, the barrel is preferably washed with hot water, brushed with "Sparkleen" (Fisher Scientific, Nepean, Ont K2E 7L6, Cat. No. 04–320) rinsed several times with deionized water, placed in methanol and sonicated for 15 minutes before being dried at 60° C.

Figure 2:
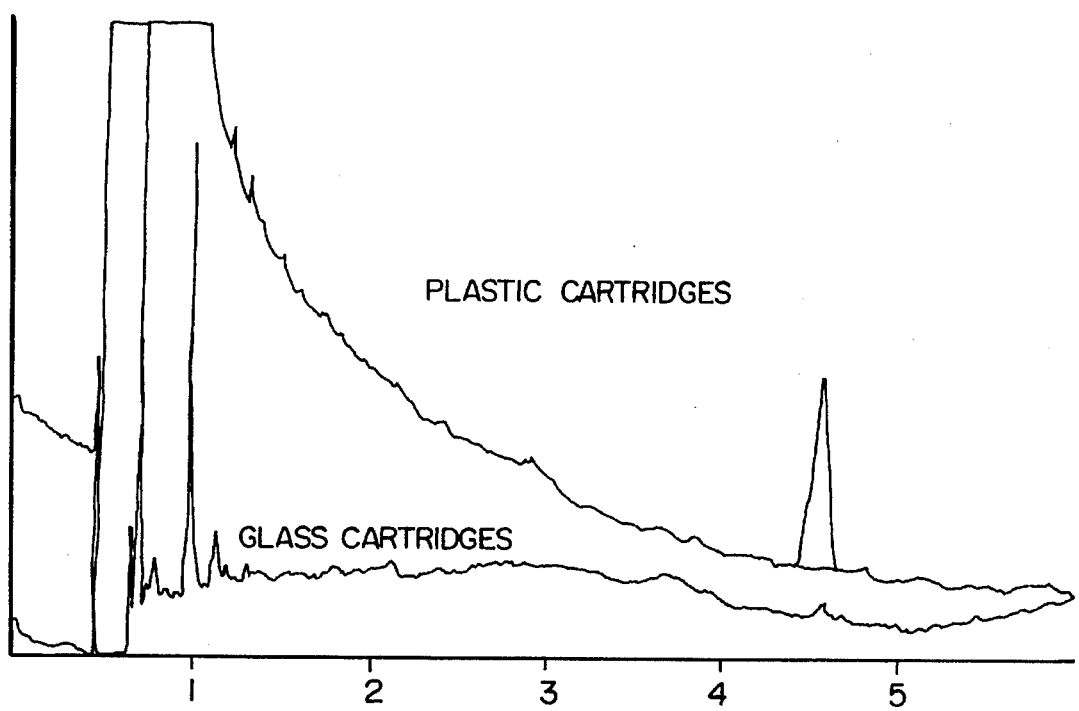
FIGS. 2 and 3 are chromatograms comparing an extraction from a column according to the present invention and commercially available columns.
Figure 3:
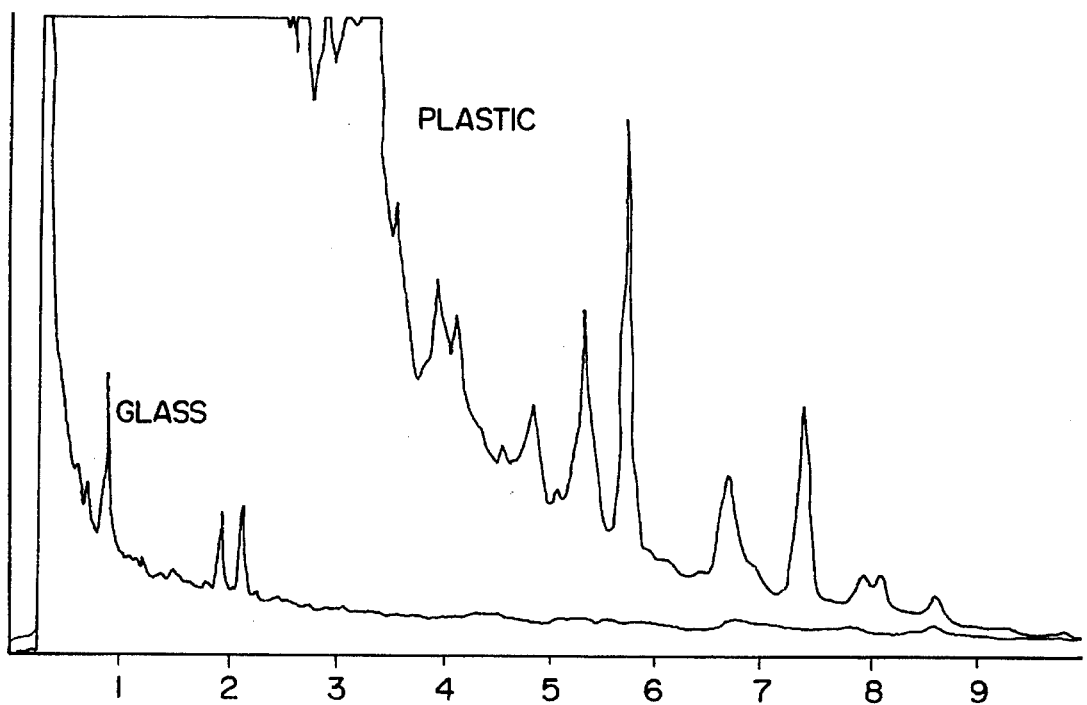

As noted above, the barrel is made from a material that does not leach materials into the biological fluids or solvents used in the extraction. All barrels made from plastics have resulted in grossly contaminated extracts, with the contaminants derived from the plastics. This is illustrated in FIGS. 2 and 3, which show that the chromatogram (attenuation of 32.0 and 64.0 for FIGS. 2 and 3, respectively) from the glass cartridge has substantially fewer peaks than those of the plastic cartridges. The plastic cartridge used in this comparison was the Merck Extrelut QE, available from EM Science, Cherry Hill, N.J. The glass cartridge used was the cartridge IX, described in Table 2a below. In both cases, 1 ml of distilled water was added to the cartridges and extracted with five 1.5 ml aliquots of chlorobutane. The extract was evaporated and reconstituted to 50 microliters with ethanol before being directly injected into a HP 5890 gas chromatograph equipped with either an electron capture detector (FIG. 3) or a nitrogen/phosphorous detector (FIG. 2) and a DB-5, 15 m×0.32 mm capillary column with 0.25 micron film thickness.

Buffer Layer

The buffer layer of the packing composition is positioned toward the inlet end of the cartridge to adjust the pH of the sample being extracted and to disperse the sample over substantially the entire diameter of the cartridge so that the sample spreads out substantially evenly into the partition layer.

The composition of the buffer layer includes buffer material for adjusting pH, and preferably an inert support. For example, the buffer layer can be composed of intermixed buffer and inert support, inert support coated with buffer or simply particles of buffer material. Any known buffer material can be used depending upon the pH desired for a particular extraction. Examples of suitable buffer materials are shown in Table 1. Many other solid organic or inorganic salts, bases and acids that dissolve readily in water but do not dissolve in the water immiscible organic solvent used for drug extraction can be also be suitable.

To achieve intermediate pH levels, the buffer materials can be dry mixed with each other before being incorporated with the inert support. All buffer materials are ACS or ANALAR grade materials.

TABLE 1

| | BUFFER | pH* |
|---|---|---|
| 1 | Oxalic acid | 1.3 |
| 2 | Tartaric acid | 2.0 |
| 3 | Citric acid | 2.1 |
| 4 | Succinic acid | 2.7 |
| 5 | Ammonium dihydrogen phosphate | 4.0 |
| 6 | Sodium dihydrogen phosphate | 4.5 |
| 7 | Potassium dihydrogen phosphate | 4.5 |
| 8 | Aluminum sulphate | 5.5 |
| 9 | Ammonium oxalate | 6.4 |
| 10 | Diammonium hydrogen phosphate | 7.9 |
| 11 | Sodium bicarbonate | 8.4 |
| 12 | Potassium bicarbonate | 9.1 |
| 13 | Disodium hydrogen phosphate | 9.1 |
| 14 | Dipotassium hydrogen phosphate | 9.1 |
| 15 | Borax | 9.2 |
| 16 | Tris(hydroxymethyl)methylamine | 10.5 |
| 17 | Sodium carbonate | 11.5 |
| 18 | Potassium carbonate | 11.5 |
| 19 | Trisodium phosphate | 12.0 |
| 20 | Tripotassium phosphate | 12.0 |

*approximate pH for an 0.1N aqueous solution

The carrier, or inert support, of the buffer layer can be made up of any solid material that has a size range that allows free flow of the liquids and that does not dissolve or in any way contaminate the aqueous sample or the organic solvent used to elute the drug. Furthermore, the carrier must not react with the buffer material. Carrier materials useful in the buffer layer include crystalline silica, glass beads, metal balls, such as stainless steel ball bearings, ceramic beads or chips, diatomaceous earth, crushed rock or washed sand. Preferably, the carrier material is crystalline silica, which has been heat treated at about 500° C. for about 3 hours to remove any contaminants. The particle size of the buffer material and the inert support is selected to ensure that the sample flows freely into the middle layer and that the entire sample is exposed to the buffer material. The particle size of the buffer material is about 100 microns to 1000 microns, preferably, from about 400 microns to 1000 microns, even more preferably, from about 600 microns to 850 microns.

The particle size of the inert support is about 200 microns to 3000 microns, preferably, from about 400 microns to 50 microns, even more preferably, from about 600 microns to 850 microns. The preferred inert support is obtained by sieving commercially available silica sand to obtain a particle size range of about 600 microns to 850 microns.

The amount of inert support and buffer material in the buffer layer can be varied. Specifically, the amounts of each component can range from about 5–50 wt % of buffer material and 95–50% inert material. Preferably, the range can be about 10–30 wt % buffer and 90–70 wt % inert material. Even more preferably, the buffer layer can be about 20 wt % buffer material and about 80% inert support.

The embodiment of the buffer layer comprising an inert support coated with the buffer material is produced in the following manner. A solution of the buffer material in water, or any other solvent in which the buffer has adequate solubility, is added to the inert support and the mixture, in the form of a slurry, stiff paste or partially wetted inert support, and is evaporated to dryness on a rotary evaporator. Care must be taken not to overheat the mixture to ensure that there is no decomposition of the buffer salt, e.g., both chemically and physically, loss of $CO_2$ from sodium bicarbonate, and that the same form of the buffer material is deposited on the inert support every time.

The following tests demonstrate that comparable results are obtained performing an extraction using a cartridge including a buffer layer that is a mixture of buffer material and inert support and an extraction using a cartridge including an inert support coated with buffer material. Specifically, the drugs diazepam and desmethyldiazepam (500 mg/ml) were extracted from plasma using basically identical cartridges; however, one cartridge contained a buffer layer comprising a mixture of 20% borax crystals and 80% silica sand, and the other cartridge contained a buffer layer comprising 20% borax coated on diatomaceous earth. Any free water was evaporated from the wet diatomaceous earth in a rotary evaporator at less than 30° C. under vacuum generated by a water aspirator.

Figure 4:
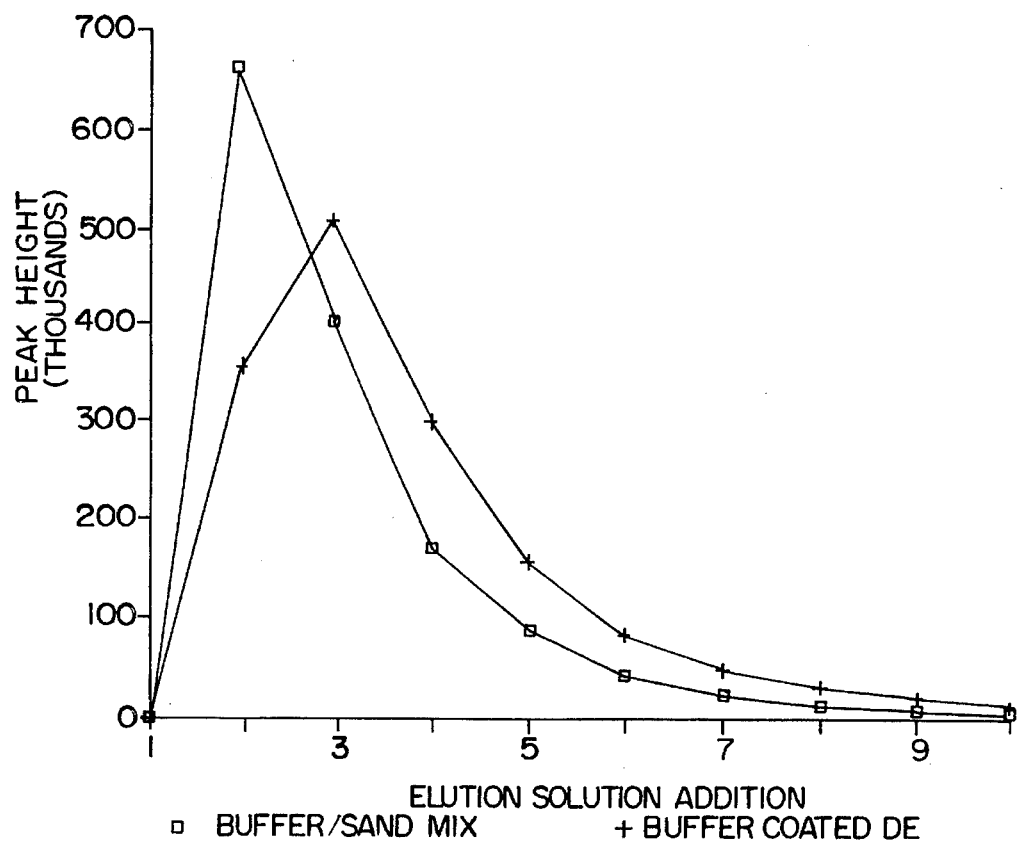
FIGS. 4 and 5 are chromatograms comparing an extraction using a buffer mixture with an extract using a coated buffer.
Figure 5:
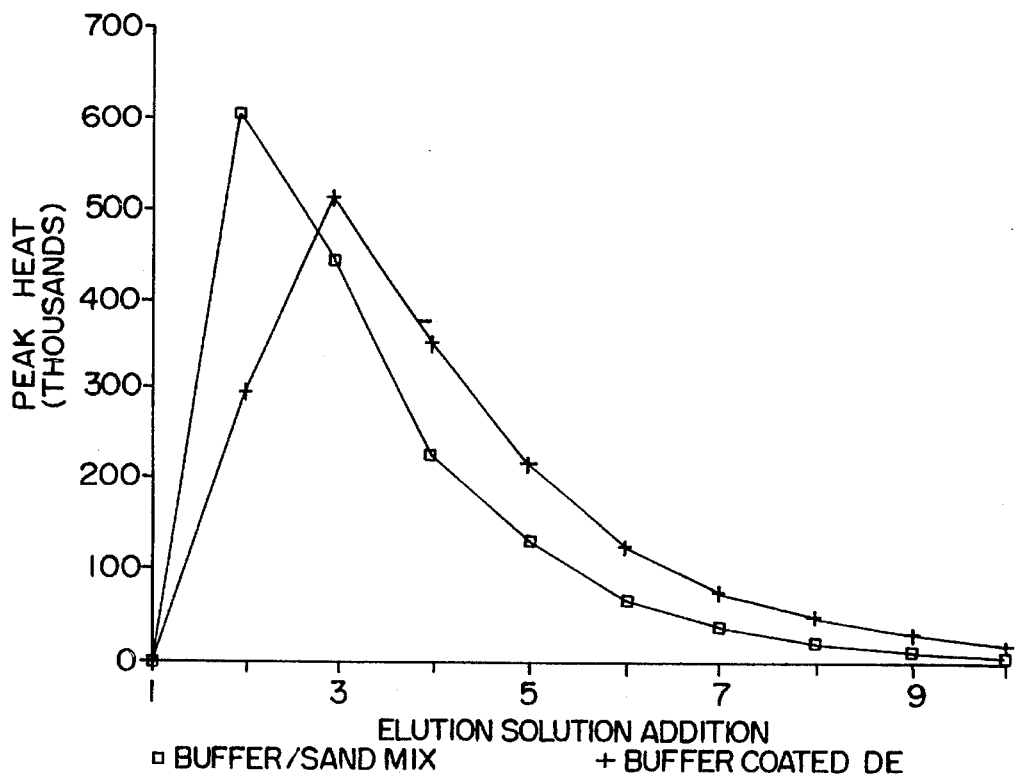

As illustrated in FIGS. 4 and 5, respectively, the elution pattern from the cartridge using a buffer layer comprising a mixture of 20% borax crystals and 80% silica sand was comparable to the elution pattern from a cartridge using a buffer layer comprising 20% borax coated on diatomaceous earth. The cartridge used in the elution illustrated in FIG. 4 included 1.19 g of buffer/sand mixture. The cartridge used in the elution illustrated in FIG. 5 included 0.51 g of buffer coated diatomaceous earth.

The other components of the cartridges were the same, including the glass syringe-type barrel available from Burdick and Jackson described above, 0.75 g of diatomaceous earth positioned below the buffer layer, 0.5 g of anhydrous sodium sulphate positioned below the diatomaceous earth, a cellulose filter positioned below the packaging composition. The cartridge that contained the buffer coated diatomaceous earth also included a 60 mesh stainless steel filter positioned above the packing composition.

The drug extracted in FIG. 4 was diazepam and in FIG. 5 was desmethyldiazepam. The extraction process used was: 1 ml of plasma extracted with 6 additions of 1.5 ml of 5% by volume ethylacetate and 95% by volume chlorobutane.

Partition Layer

Positioned below the buffer layer is a layer of material for spreading the sample, whose pH has been adjusted by the buffer layer, into a thin-film over an inert support. Any material that is inert, highly porous, and includes a large surface area can be used for the partition layer. Specifically, materials that can be used for the this partition layer include silica gel, fibrous materials made of cellulose or glass, and diatomaceous earth. Preferably, the partition layer is composed of diatomaceous earth with large surface area.

The particle size of the partition layer assures free flow of the sample with a minimum of channelling. The particle size can range from about 100 to 3000 microns, preferably, from about 200 to 1000 microns, even more preferably, from about 600 to 850 microns. A large percentage of particles of less than about 200 microns would lead to reduced flow, necessitating much longer total processing times.

A preferred diatomaceous earth for use in the thin film layer is Hydromatrix available from Varian Associates, Sunnyvale, Ca, Cat. No. AL-001980-03. This diatomaceous earth is sieved to remove particles outside the range useful in the partition layer. The selected material, with a particle size range greater than 600 microns, is heat treated in a standard muffle furnace, with air atmosphere, for about 3 hours at about 500° C. to remove all organic materials that could be extracted from the column and cause interference during analysis.

Additional Layer

The additional layers of the packing composition can have various functions. For example, the layers can remove any water that remains in the eluate, the layers can remove any additional extraneous materials, and/or the layers can derivatize the drug that is being extracted. For example, the additional layers can include a layer of drying agent for removing any moisture from the eluate. Any material that absorbs water and does not contaminate the eluate can be used, such as anhydrous sodium sulphate, anhydrous magnesium perchlorate, anhydrous calcium sulphate, copper sulphate and alumina. Preferably, ACS grade anhydrous sodium sulphate heated at about 500° C. for about three hours to remove any contaminants is used as the drying agent. The particle size of the drying agent can be about 100 microns to 1000 microns, preferably, about 200 microns to 1000 microns, even more preferably about 400 to 850 microns.

While the additional layers have been shown in the preferred embodiment to be the lowermost layers, the additional layers can be positioned at various locations in the cartridge depending upon the extraction. For example, the additional layers can be placed above the buffer layer or between the buffer layer and the partition layer. Furthermore, the additional layers can be included in more than one location.

Frits/Filters

The packing composition is held within the barrel by frits or filters, (hereinafter collectively referred to as "filters") positioned above and below the packing composition. The filter positioned at the bottom of the packing composition prevents fines from the packing composition from entering the collection tube where they could cause clogging problems when the reconstituted extract is being sampled. The bottom filter can be made from any material that does not add contaminants to the eluate and allows the eluate to flow from the cartridge, such as cellulosic material, stainless steel mesh, glass, porous polyolefins, porous polytetraflouroethylene, fine cloth held by a plastic ring or glass fiber mat. Preferably, the bottom filter is made from cellulose. Even more preferably, the bottom filter is a precut, cellulosic filter, type 740-E, from Schleicher and Schuell, available from Canlab Scientific Products Cat. No. F2755-2, which is preferably washed with ethyl acetate and dried with a stream of nitrogen. Cellulose is the preferred material for making the filter because the undesirable cleanliness, cost and flow/ wetting characteristics of the other materials are inferior to those of cellulosic materials. The filter is dimensioned to fit snugly within the inner diameter of the barrel.

The filter on top of the packing composition retains the packing during transportation to prevent mixing of the layers. Additionally, the top filter distributes the sample uniformly over the whole diameter of the cartridge. The top filter can be made from stainless steel mesh, random glass fiber mat or cellulosic filter materials. The preferred material is a stainless steel plain weave mesh, with a mesh opening size of about 0.070 inches. As with the bottom filter, the top filter is dimensioned to fit snugly within the inner diameter of the cartridge. The top filter can be held in place by the constriction in the cartridge wall if it has sufficient stiffness and flexibility that it can be pushed past the constriction without permanent distortion. Other ways that the top filter can be positioned are by the insertion of a tightly fitting ring of a flexible material immediately after the filter disc, or an application of a bead of adhesive immediately above the filter which will adhere tightly to the glass. However, the materials must be chosen so as to eliminate the possibility of introducing extraneous materials which would be extracted.

Examples of cartridges that have been used for the isolation of drugs from human plasma samples are defined in Table 2a. Each cartridge is substantially similar except for the buffer layer, which is listed in Table 2a. The cartridges used in the examples each include about 1.0 gram of a buffer layer, about 0.75 grams of a partition layer comprising heat treated, sieved diatomaceous earth, and about 0.5 gram of a drying layer including sodium sulphate. The barrel used was the glass syringe type barrel available from Burdick and Jackson, described above. The bottom filter was the cellulosic filter from Schleicher and Schuell (Type 740-E). The amount of each layer can be varied depending on the size of the cartridge and the type of extraction.

TABLE 2a

| Cartridge type | Approx. pH | Type of Buffer | Wt % Buffer/crystalline silica |
|---|---|---|---|
| IX | 9 | Borax | 20/80 |
| XI | 11 | Tris* | 20/80 |
| VIII | 8 | Sodium Bicarbonate | 30/70 |
| III | 3 | Citric Acid | 20/80 |

*tris(hydroxymethyl)methylamine

The method of extracting a substance from a biological fluid according to the present invention involves the following steps.

A particular cartridge containing a particular buffer mixture, is selected depending upon the chemical properties of the drug being extracted. More specifically, most drugs have one or more functional groups which makes them either acid, basic or amphoteric. If a drug has basic characteristics, it will readily pick up a proton (H+); if it is acidic, it will lose a proton. In both instances, a charged species is formed from an electrically uncharged molecule. In aqueous solution, depending on the pH, the drugs can be present in the charged form which is a highly water soluble state or in the uncharged form which is more soluble in the organic solvent. A particular cartridge is chosen with the goal of putting the drug molecule in the aqueous sample in the uncharged state by selecting the pH of the cartridge buffer to facilitate extraction with an organic solvent.

Thus, an alkaline drug requires a high pH to prevent charge formation, and Cartridge No. IX or No. XI would be appropriate for extracting alkaline drugs. An acid drug requires a low pH, to prevent its dissociation, since there are already many protons in solution and, accordingly, Cartridge No. III would be appropriate. Amphoteric drugs can behave both as a base and as an acid; it is therefore necessary to react one of the functional groups with special reagents, e.g., alkyl sulfonates and tetrabutyl ammonium phosphate as reagents for acidic and basic functional groups, respectively. Such special reagents can be added to the sample and/or can be included in one or more layers of the multilayer packing composition in the cartridge.

The process of extraction begins by adding a measured aliquot of biological fluid containing a drug to be extracted to the cartridge. The fluid flows through the buffer layer and spreads out in a thin film over the partition layer. The fluid does not elute from the cartridge, nor are any materials washed off prior to elution of the drug.

After a period of time, from about 1 minute to 30 minutes, preferably about 5 to about 15 minutes, even more preferably about 10 minutes, a first measured aliquot of organic solvent is added, and the eluate is collected. The solvent addition process is repeated for about 5 or 6 times, at intervals from about 1 minute to 20 minutes, preferably about 3 to 10 minutes, even more preferably about 5 minutes. All of the eluates are combined in a collection tube.

Examples of organic solvents that can be used include pentane, hexane, cyclohexane, heptane, iso-propyl ether, chlorobutane, carbon tetrachoride, methylene chloride, chloroform, diethyl ether, toluene or ethylacetate. These solvents can be used on their own or in mixtures of two or more in order to achieve selectivity for the extraction of the drug from a particular matrix. Specifically, it has been found that a small amount of ethylacetate (EtAC) added to any of the solvents listed above can improve the extraction efficiency and selectivity. The amount of EtAC in the solvent mixture can be up to 50% by volume. Preferably, the amount of EtAC in the solvent mixture is about 5–10% volume.

The selection of a particular solvent or solvent mixture for a particular extraction is made through a series of experiments. Different types of cartridges and internal standards may also be evaluated with each of the different solvents chosen. All extracts collected are then analyzed by the same analytical technique. In this way, the solvent which gives the cleanest extract with the best recovery of the drug can be selected.

The solvent is evaporated from the collection tube using any known evaporation technique and the non-volatile drug is re-dissolved in a small aliquot of a strong, polar solvent, such as methanol, ethyl acetate or ethanol. Samples from this concentrated drug solution are directly injected into a GC, HPLC or LC/MS or other analytical system.

This method is performed using gravity elution without suction or pressure that is usually applied with solid phase cartridges, and without any pretreatment of the cartridges. Also, the aqueous phase and substantially all contaminants are left on the column. The column contents can be discarded and the barrel recycled.

There are several important parameters that must be carefully controlled for optimum results. Adequate time must be allowed for the biological fluid to penetrate and spread in a thin film over the partition layer. The porosity/absorbtivity of this layer must be controlled so that the sample spontaneously spreads over about 70% of the layer. Further, adequate time must be allowed between elutions with the organic solvent for re-equilibration to take place effectively. An equilibrium is established between the drug in the aqueous layer and the organic solvent which depends on the relative solubility of the drug in the two media. A portion of the solvent from the first addition is retained on the spreading layer. Each time more solvent is added, the "old" solvent into which more drug has solubilized is flushed out and replaced with the fresh solvent that has been added. In this way, the drug is progressively removed from the aqueous layer. If sufficient time is not allowed between additions of solvent, the solvent retained on the spreading layer will not effectively solubilize the drug, and recovery will be lower and variable.

The process according to the present invention is illustrated in the following non-limiting examples. For each example the following information is provided:

a) A table summarizing details of the analytical conditions and including the recoveries achieved at three concentration levels;

b) A table including a full set of data to establish the between run precision and accuracy for the analysis of these drugs in human plasma, wherein the nominal value is the actual concentration of drug in a sample; the mean is the mean concentration calculated from n actual measurements of sample; SD is the standard deviation of the mean; mean as percent of nominal is mean/nominal×100; CV % is SD/mean×100; and n is the number of measurements;

c) A chromatogram obtained from the extraction of blank samples, i.e., no drug is injected, the region of the chromatogram where the drug would appear must not exhibit any interference peaks;

d) A chromatogram of an extract from a sample that includes a low level of the drug to be extracted, which can be as low as 50 picogram per milliliter; and e) A chromatogram of an extract from a sample including an intermediate level of the drug to be extracted. Standard laboratory methods are used to obtain the statistical data.

EXAMPLE 1

Example 1 illustrates the extraction of the drug buspirone using extraction cartridge IX defined above. The extraction conditions, including volume of plasma added, internal standard, extraction solvent, volume of extraction solvent, volume of reconstitution solvent, and the chromotography conditions for Examples 1–4 are summarized in Table 2b.

Figure 6:
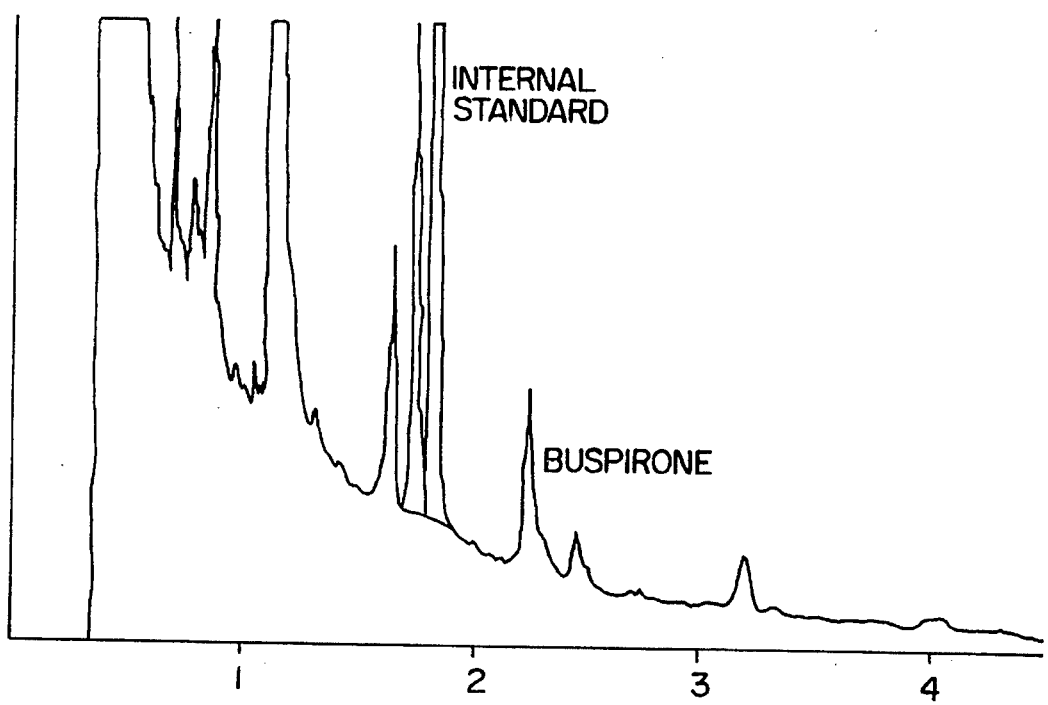
FIGS. 6–17 chromatograms of materials extracted according to the present invention.
Figure 7:
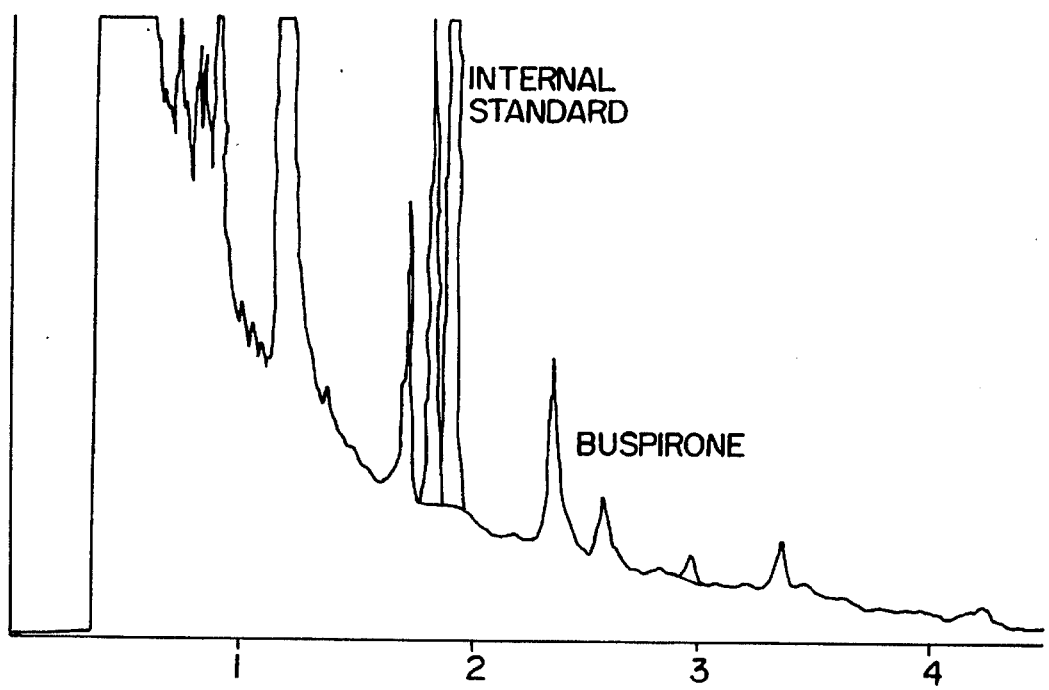
Figure 8:
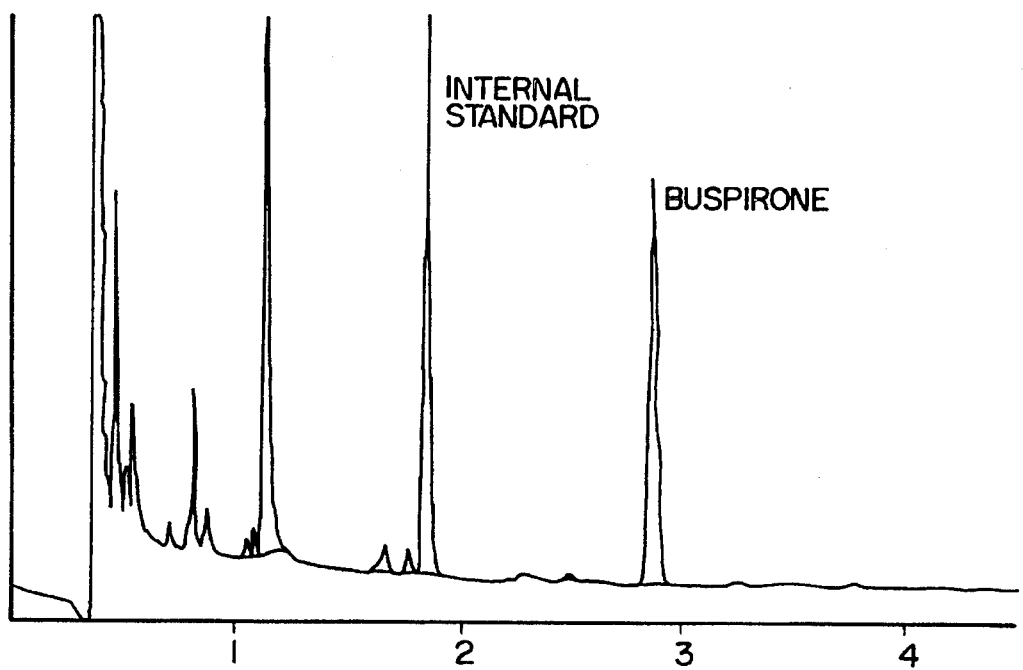

In addition to the plasma and internal standard, approximately 0.3% wt. of the anticoagulant ethylene diamine tetraacetic acid (EDTA) is added in each of Examples 1–4. The analytical method is summarized in Table 3. The results are summarized in Table 4. FIGS. 6–8 are chromatograms (attenuation 16.0, 16.0 and 100.0, respectively) of buspirone samples extracted according to the present invention at 0.00 pg/ml, 50.00 pg/ml and 8000.00 pg/ml respectively.

EXAMPLE 2

Figure 9:
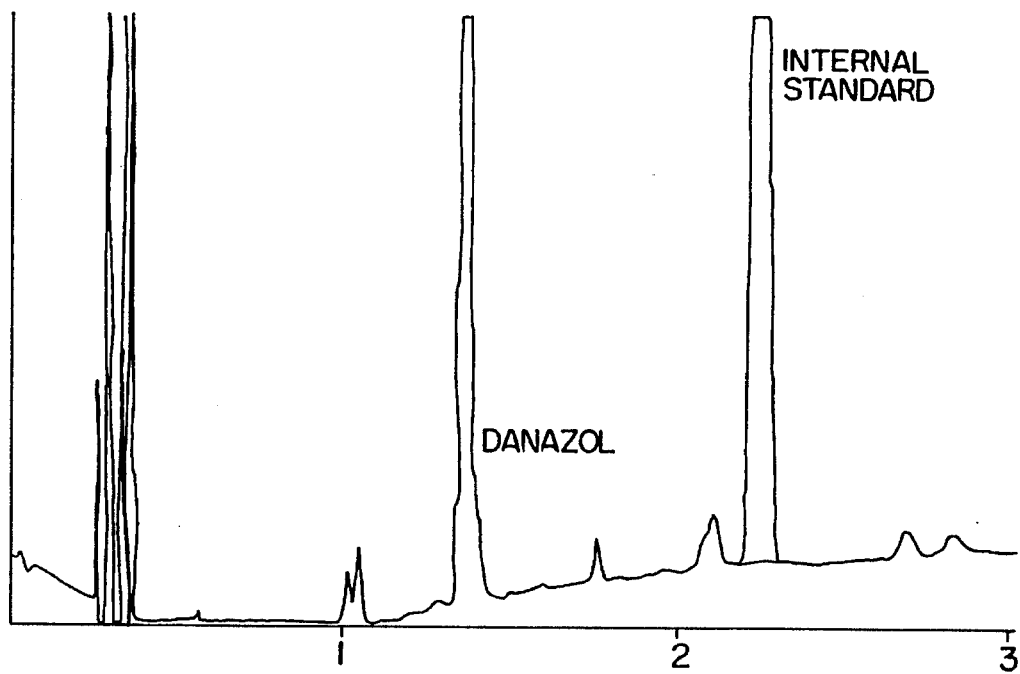
Figure 10:
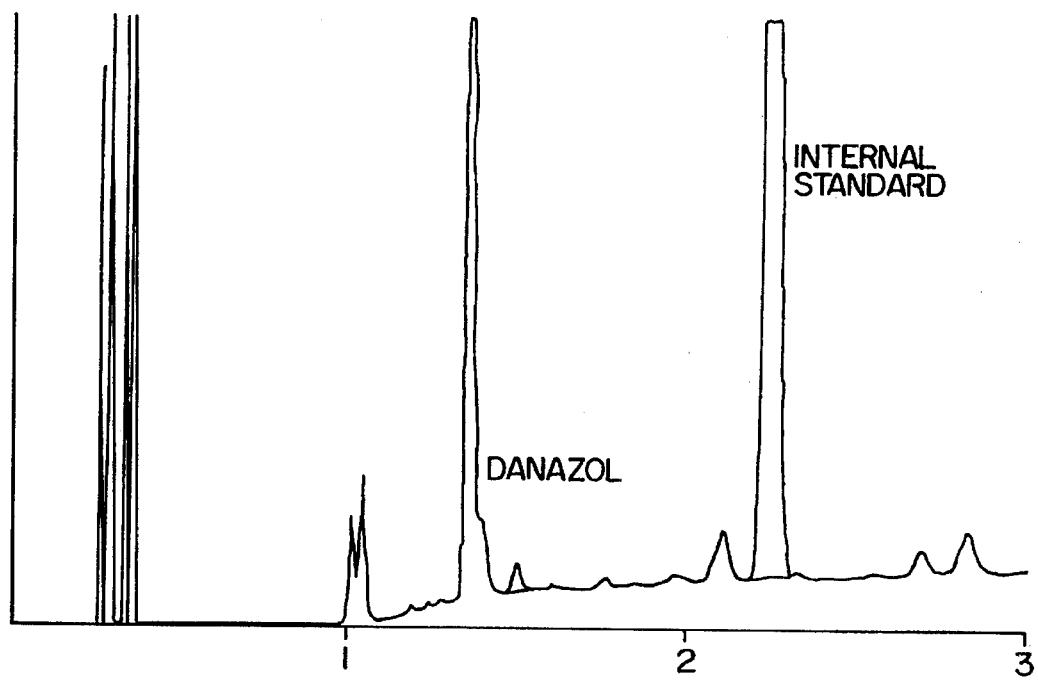
Figure 11:
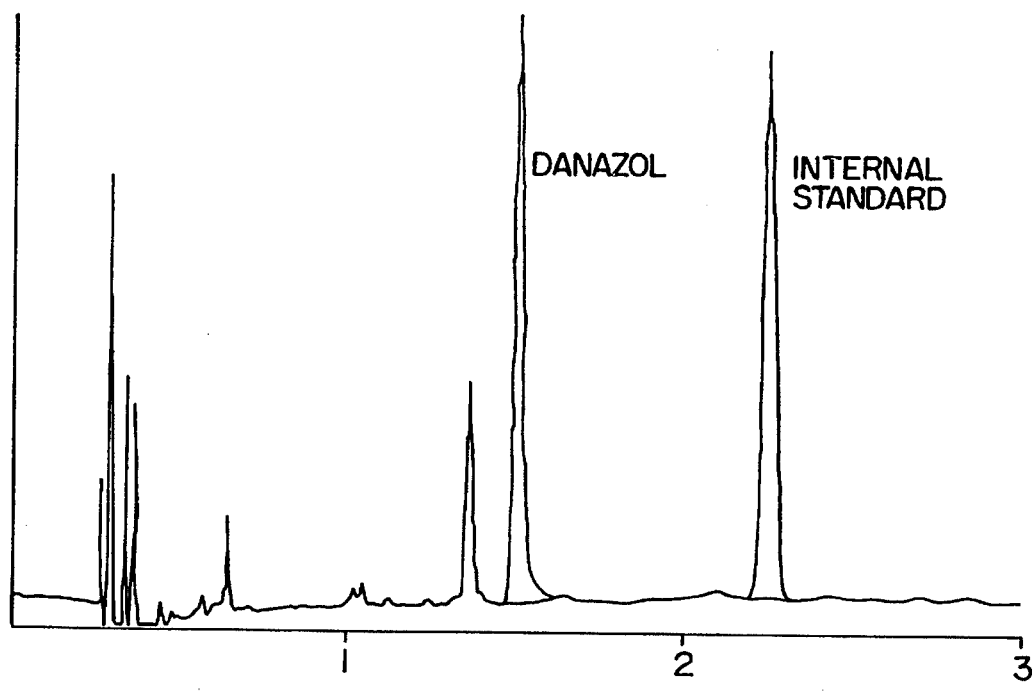

Example 2 illustrates the extraction of the drug danazol, at a variety of concentration levels, using extraction cartridge IX. As noted above, the details of the extraction and the chromatography conditions are summarized in Table 2b. The analytical method is summarized in Table 5. The results are summarized in Table 6. FIGS. 9–11 are chromatograms (attenuation of 64.0, 64.0 and 240.0, respectively) of danazol samples extracted according to the present invention at 0.00 ng/ml, 2.03 ng/ml and 248.25 ng/ml respectively.

EXAMPLE 3

Figure 12:
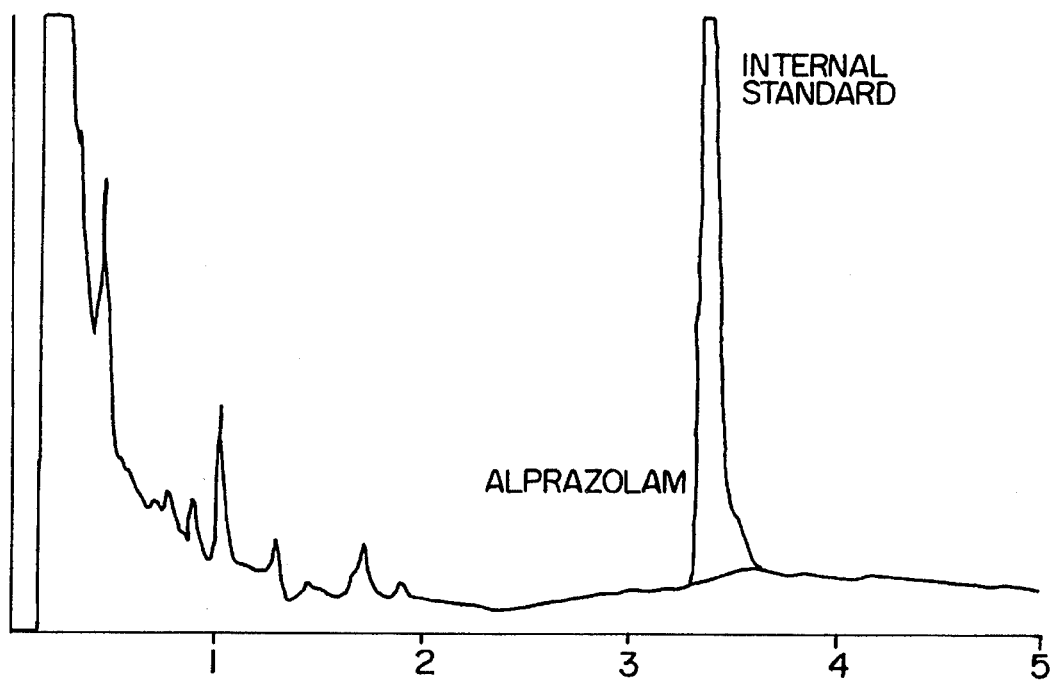
Figure 13:
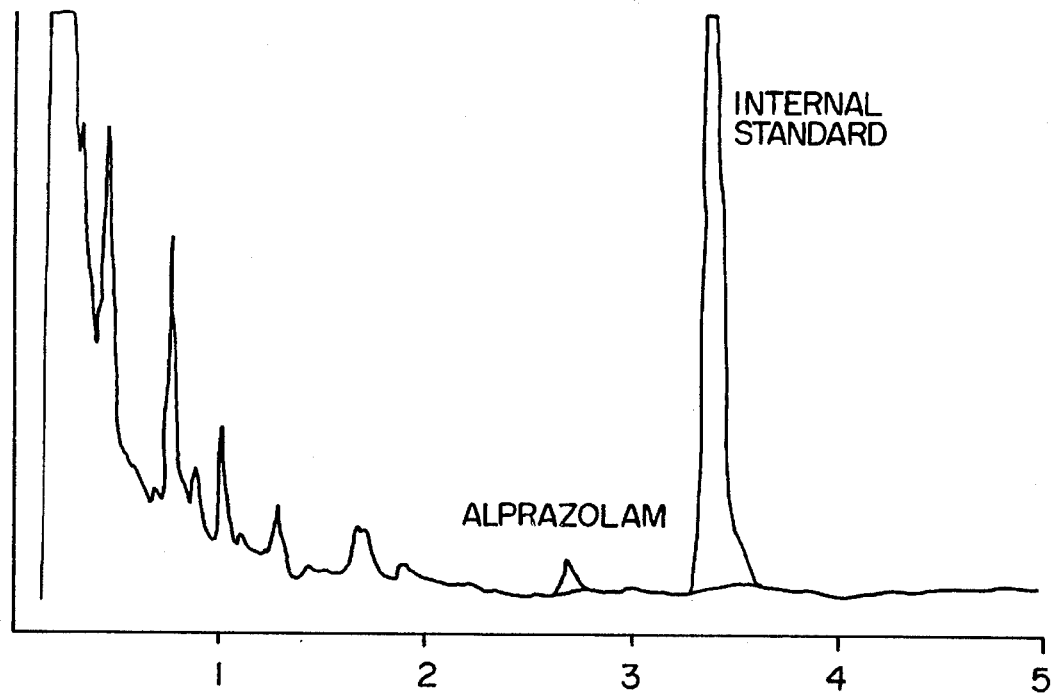
Figure 14:
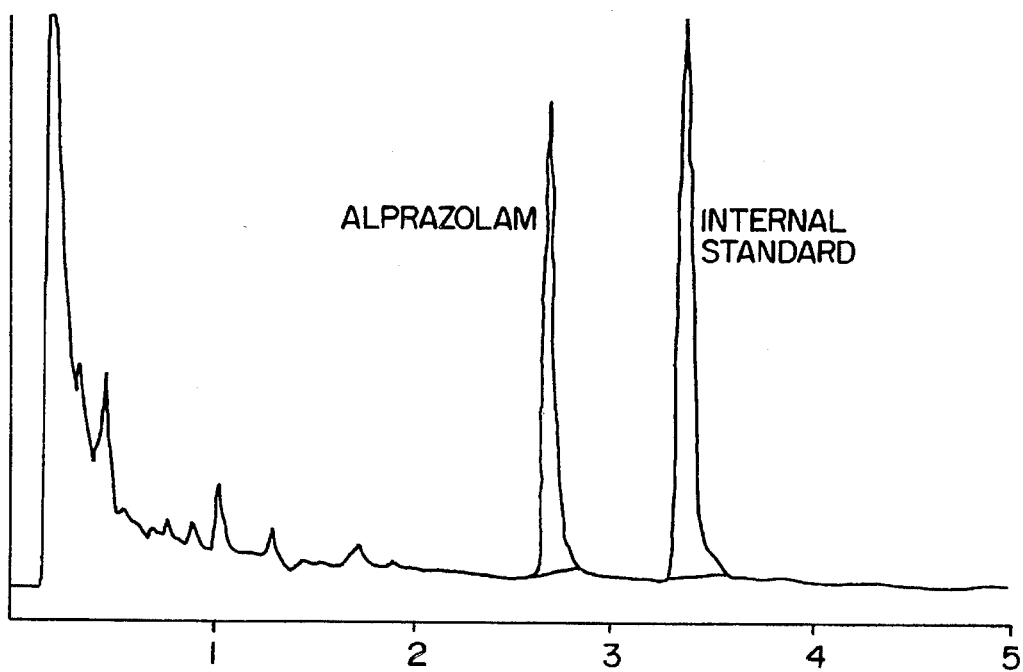

Example 3 illustrates the extraction of the drug alprazolam, at a variety of concentration levels, using an extraction cartridge IX. The details of the extraction and the chromotography conditions are summarized in Table 2b. The analytical method is summarized in Table 7. The results are summarized in Table 8. FIGS. 12–14 are chromatograms (attenuation of 64.0, 64.0 and 170.0, respectively) of alprazolam samples extracted according to the present invention at 0.00 ng/ml, 0.50 ng/ml and 16.00 ng/ml respectively.

EXAMPLE 4

Figure 15:
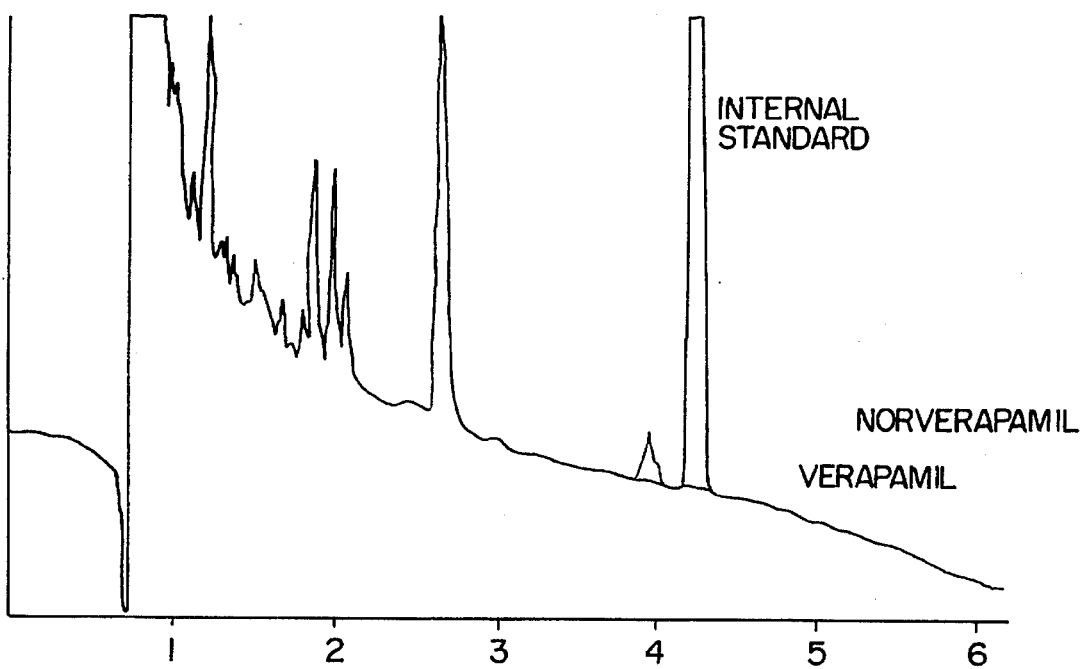
Figure 16:
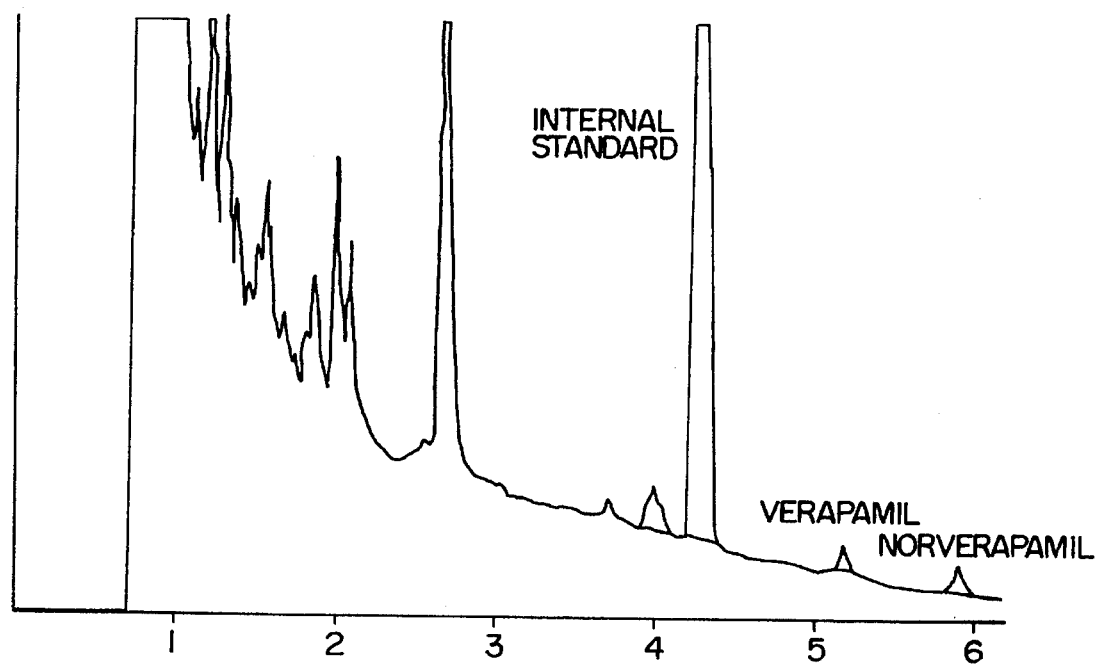
Figure 17:
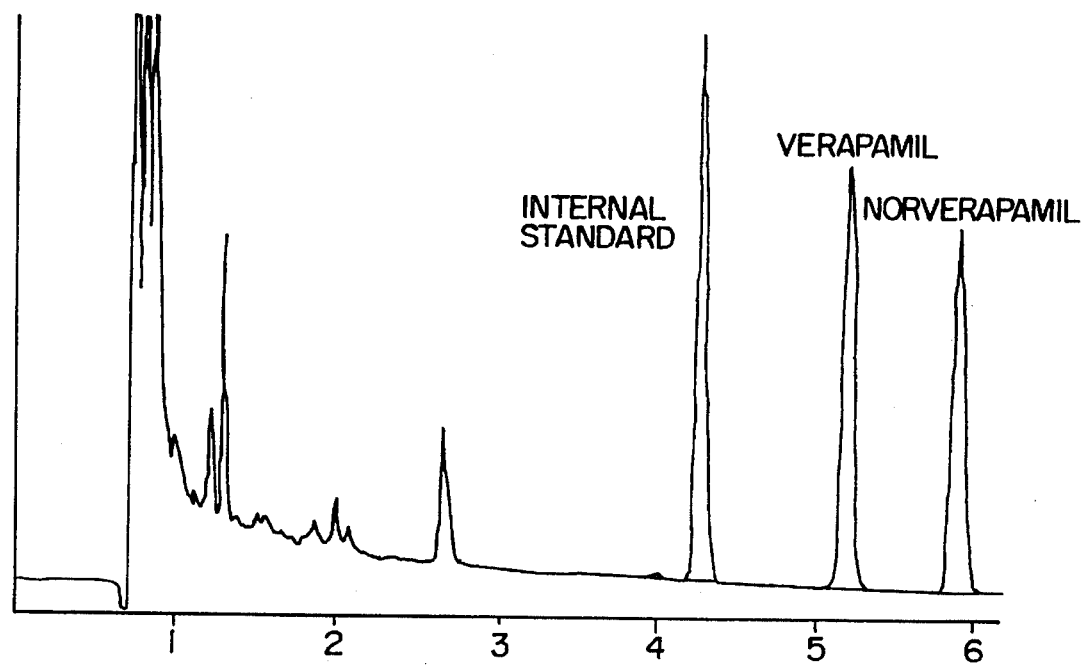

Example 4 illustrates the extraction of the drugs verapamil and norverapamil, at a variety of concentration levels, using an extraction cartridge IX. The details of the extraction and chromatography conditions are summarized in Table 2b. The analytical method is summarized in Table 9. The results are summarized in Tables 10 and 11. FIGS. 15–17 are chromatograms (attenuation of 64.0, 64.0 and 400.0, respectively) of verapamil and norverapamil samples extracted according to the present invention at 0.00 ng/ml, for each of verapamil and norverapamil 2.00 ng/ml and 201.11 ng/ml verapamil and 209.59 ng/ml for each of verapamil and norverapamil norverapamil respectively.

EXAMPLE 5

Figure 17A:
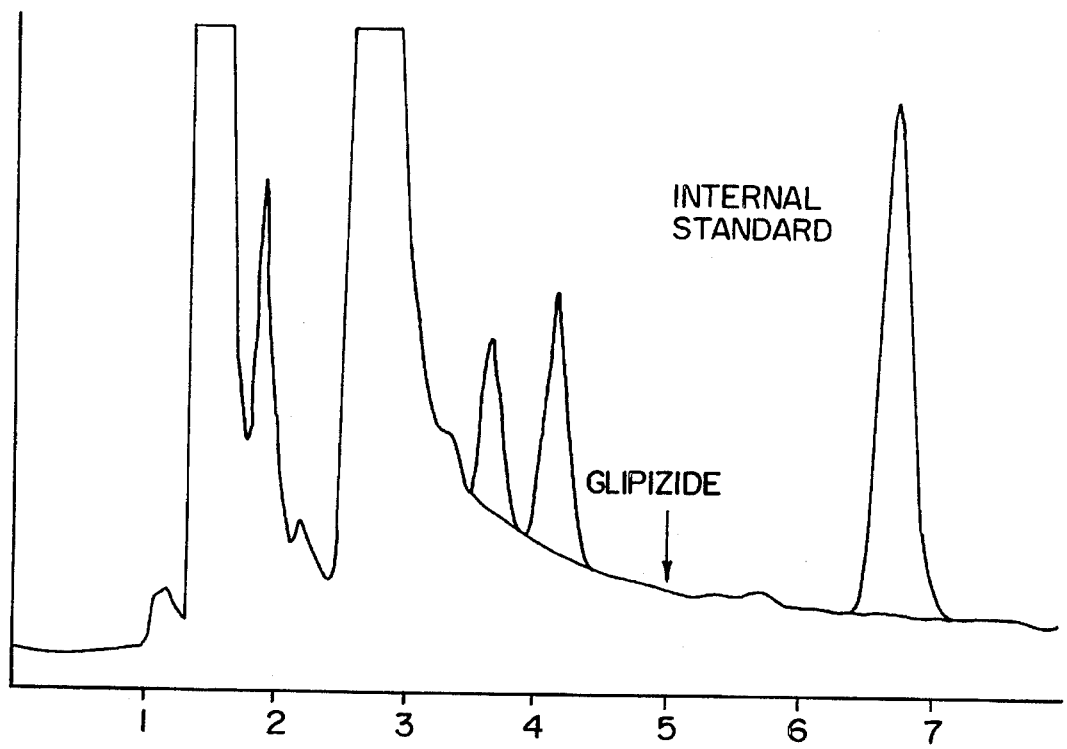
FIGS. 17a, 17b and 17c are chromatograms of materials extracted according to the present invention.
Figure 17B:
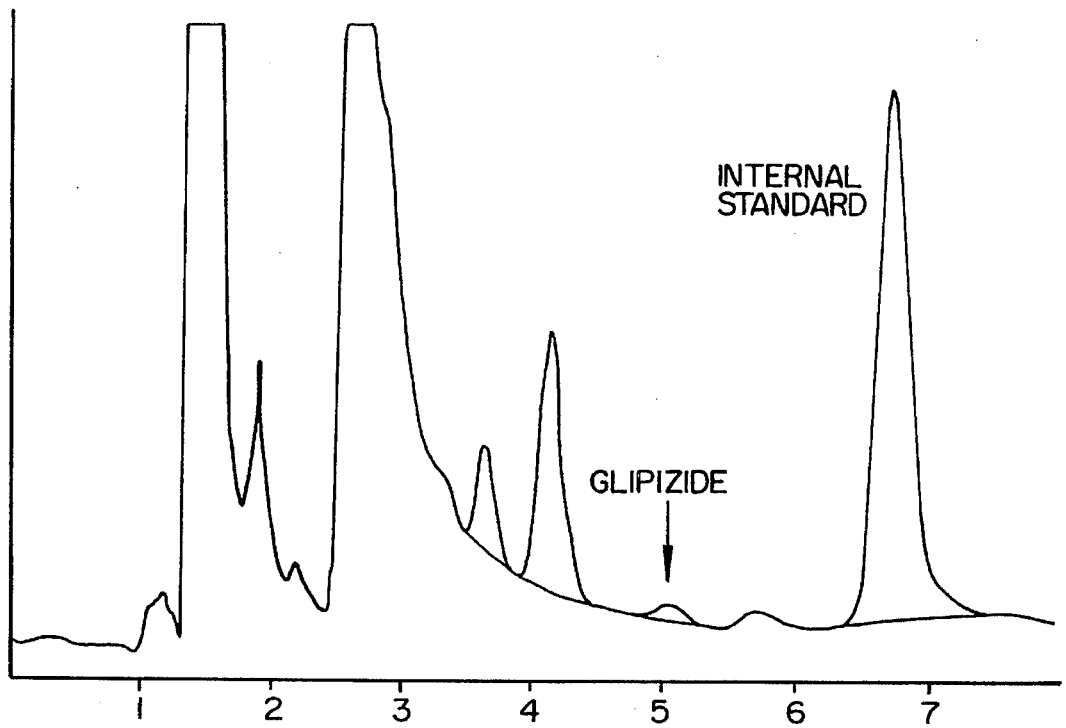
Figure 17C:
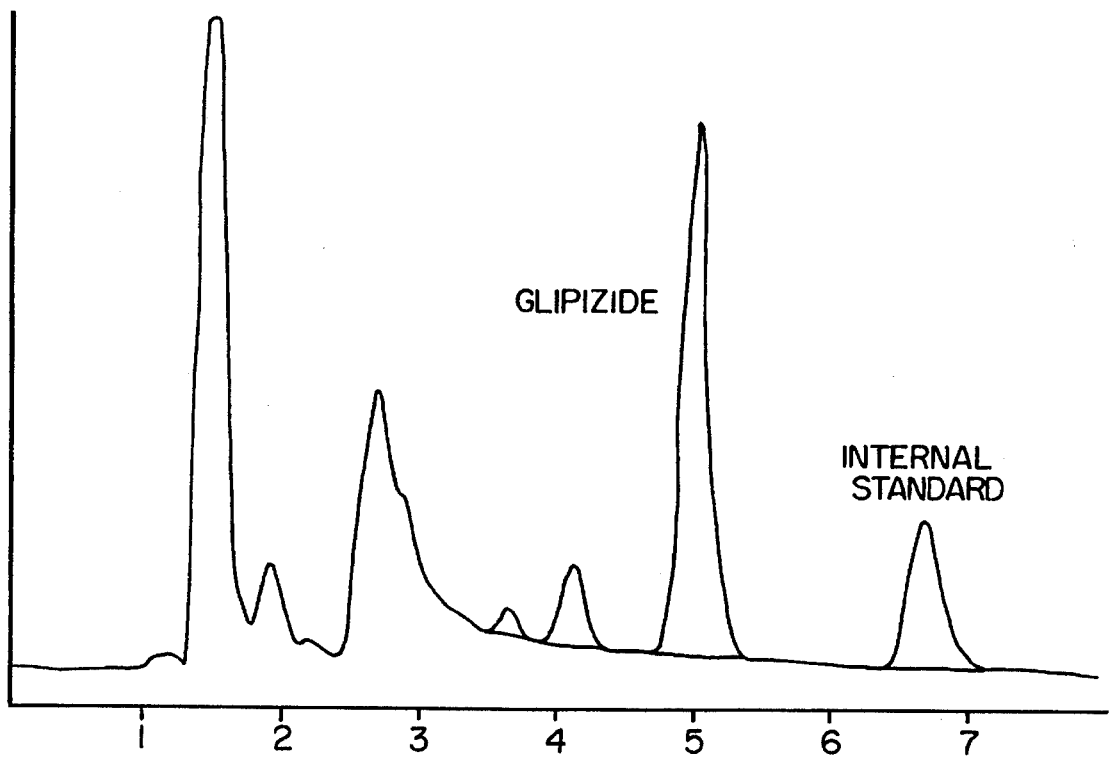

Example 5 illustrates the extraction of the drug glipizide, at a variety of concentration levels using an extraction cartridge III. The details of the chromatography conditions are summarized in Table 2b. The analytical method is summarized in Table 12. FIGS. 17a–17c are chromotograms (attenuation of 32.0, and 32.0 and 160.0, respectively) of glipizide samples extracted according to the present invention at 0.00 mg/ml, 15.0 mg/ml and 800 mg/ml.

TABLE 2b

Extraction and Chromatographic Conditions for Examples 1–5

|  | Buspirone Example 1 | Verapamil Norverapamil Example 4 | Danazol Example 2 | Alprazolam Example 3 | Glipizide Example 5 |
|---|---|---|---|---|---|
| Volume of Plasma | 1.0 ml | 1.0 ml | 1.0 ml | 1.0 ml | 1.0 ml |
| Internal Standard | Loratadine | Loratadine | Loratadine | Triazolam | Alprazolam |
| Extraction Solvent | 5% ethyl acetate in chlorobutane | 5% ethyl acetate in isopropyl ether | 5% ethyl acetate in hexane | 5% ethyl acetate in chlorobutane | 5% ethyl acetate in methylene chloride |
| Volume of solvent | 5 × 1.5 ml | 5 × 1.5 ml | 5 × 1.5 ml | 5 × 1.5 ml | 5 × 1.5 ml |
| Volume of reconstitution solution | 25 microliter (mcl) of methanol | 25 microliter of denatured alcohol | 50 mcl of ethyl acetate | 50 mcl of ethyl acetate | 50 mcl methanol |
| Capillary column | DB-5, 15 m × 0.32 mm 0.25 micron film thickness | | | DB 17, 7.5 m × 0.25 mm; 0.25 micron film thickness | DB-5, 15 m × 0.32 mm 0.25 micron film thickness |
| Detector | Nitrogen/Phosphorous | | | Electron capture | Nitrogen/Phosphorus |
| Oven temp. | 255° C. | 260° C. | 262° C. | 280° C. | 300° C. |
| Injector temp. | 325° C. | 300° C. | 300° C. | 310° C. | 400° C. |
| Detector temp. | 300° C. | 275° C. | 300° C. | 325° C. | 300° C. |

Type of chromatograph: HP 5890 equipped with split/splitless capillary injection port; automatic liquid sampler; integrator data system

TABLE 3

SUMMARY OF THE BUSPIRONE ANALYTICAL METHOD

| Matrix | Plasma |
|---|---|
| Volume Required | 1.0 ML |
| Anticoagulant | EDTA |
| Extraction Cartridge | Cartridge IX |
| Concentration Range | 50.0–10009.0 pg/ml |
| Chromatography | High resolution capillary column |
| Detection Mode | NPD |
| Quantitation Method | Internal Standard Method |
| Quantitation by | Peak height ratio |
| Regression | Linear |
| Goodness of Fit | The correlation coefficients were better than or equal to 0.9950 |
| Recovery | 73.8% at 300.00 pg/mL |
|  | 63.2% at 2500.00 pg/mL |
|  | 64.9% at 8000.00 pg/mL |
| Stability | Stable at room temperature in plasma for 8 hours. |
|  | Stable in plasma after three freeze-thaw cycles. |
|  | Stable in injection solvent for 6.5 hours |

TABLE 4

BETWEEN-RUN PRECISION AND ACCURACY FOR BUSPIRONE IN HUMAN PLASMA

| Samples | Nominal Value (pg/mL) | Mean ± SD (pg/mL) | Mean as % of Nominal | CV % | n |
|---|---|---|---|---|---|
| A | 50.0 | 51.4 ± 4.84 | 102.8% | 9.4% | 9 |
| B | 300.0 | 270.6 ± 26.67 | 90.2% | 9.9% | 9 |
| C | 2500.0 | 2238.1 ± 61.34 | 89.5% | 2.7% | 8 |
| D | 8000.0 | 7701.4 ± 500.28 | 96.3% | 6.5% | 8 |
| E | 50.0 | 50.7 ± 2.87 | 101.4% | 5.7% | 5 |
| F | 100.1 | 101.5 ± 5.19 | 101.4% | 5.1% | 5 |
| G | 500.5 | 483.8 ± 13.66 | 96.7% | 2.8% | 4 |
| H | 1501.4 | 1497.0 ± 96.77 | 99.7% | 6.5% | 5 |
| I | 5004.6 | 4922.4 ± 404.60 | 98.4% | 8.2% | 5 |
| J | 7506.8 | 7858.5 ± 210.13 | 104.7% | 2.7% | 3 |
| K | 9008.2 | 9171.4 ± 680.39 | 101.8% | 7.4% | 5 |
| L | 10009.0 | 9732.7 ± 366.93 | 97.2% | 3.8% | 5 |

TABLE 5

SUMMARY OF THE DANAZOL ANALYTICAL METHOD

| Matrix | Plasma |
|---|---|
| Volume Required | 1.0 ml |
| Anticoagulant | EDTA |
| Extraction Cartridge | Cartridge IX |
| Concentration range | 2.03–400.40 ng/ml |
| Chromatography | High resolution capillary column |
| Detection Mode | NPD |
| Quantitation Method | Internal Standard Method |
| Quantitation by | Peak Height Ratio |
| Regression | Log polynomial |
| Goodness of fit | The correlation coefficients were better than or equal to 0.9990 |
| Recovery | 87.2% at 4.97 ng/mL |
|  | 88.1% at 79.44 ng/mL |
|  | 87.4% at 248.25 ng/mL |
| Stability | Stable at room temperature in plasma for 8.5 hours |
|  | Stable in plasma after three freeze-thaw cycles |
|  | Stable in injection solvent for 8 hours |

TABLE 6

BETWEEN-RUN PRECISION AND ACCCURACY FOR DANAZOL IN HUMAN PLASMA

| Samples | Nominal Value (pg/mL) | Mean ± SD (pg/mL) | Mean as % of Nominal | CV % | n |
|---|---|---|---|---|---|
| A | 2.03 | 2.05 ± 0.233 | 100.8% | 11.4% | 17 |
| B | 4.97 | 4.90 ± 0.547 | 97.5% | 11.2% | 24 |
| C | 79.44 | 77.45 ± 7.494 | 96.5% | 9.7% | 25 |
| D | 248.25 | 259.76 ± 19.063 | 103.6% | 7.3% | 23 |
| E | 2.00 | 2.03 ± 0.119 | 101.6% | 5.9% | 13 |
| F | 4.00 | 3.89 ± 0.305 | 97.2% | 7.8% | 10 |
| G | 10.01 | 10.04 ± 0.527 | 100.3% | 5.3% | 13 |
| H | 50.05 | 51.38 ± 4.164 | 102.7% | 8.1% | 11 |
| I | 100.10 | 98.73 ± 5.836 | 98.6% | 5.9% | 12 |
| J | 200.20 | 203.65 ± 11.877 | 101.7% | 5.8% | 11 |
| K | 300.30 | 297.66 ± 20.658 | 99.1% | 6.9% | 13 |
| L | 400.40 | 400.72 ± 18.352 | 100.1% | 4.6% | 11 |

TABLE 7

SUMMARY OF THE ALPRAZOLAM ANALYTICAL METHOD

| | |
|---|---|
| Matrix | Plasma |
| Volume Required | 1.0 ml |
| Anticoagulant | EDTA |
| Extraction Cartridge | Cartridge IX |
| Concentration range | 0.500–20.000 ng/ml |
| Chromatography | High resolution capillary column |
| Detection Mode | ECD |
| Quantitation Method | Internal Standard Method |
| Quantitation by | Peak Height Ratio |
| Regression | Ln polynomial |
| Goodness of fit | The correlation coefficients were better than or equal to 0.9920 |
| Recovery | 72.1% at 1.406 ng/mL |
| | 72.9% at 8.032 ng/mL |
| | 74.5% at 16.064 ng/mL |
| Stability | Stable at room temperature in plasma for 6 hours |
| | Stable in plasma after three freeze-thaw cycles |
| | Stable in injection solvent for 7.5 hours |

TABLE 8

BETWEEN-RUN PRECISION AND ACCURACY FOR ALPRAZOLAM IN HUMAN PLASMA

| Samples | Nominal Value (pg/mL) | Mean ± SD (pg/mL) | Mean as % of Nominal | CV % | n |
|---|---|---|---|---|---|
| A | 0.50 | 0.59 ± 0.036 | 117.7% | 6.1% | 6 |
| B | 1.41 | 1.36 ± 0.103 | 96.5% | 7.6% | 44 |
| C | 8.03 | 8.32 ± 0.390 | 103.5% | 4.7% | 46 |
| D | 16.06 | 16.12 ± 1.017 | 100.3% | 6.3% | 46 |
| E | 0.50 | 0.52 ± 0.018 | 103.6% | 3.5% | 23 |
| F | 1.00 | 0.95 ± 0.055 | 94.6% | 5.8% | 22 |
| G | 4.00 | 3.98 ± 0.164 | 99.6% | 4.1% | 23 |
| H | 6.00 | 6.19 ± 0.268 | 103.2% | 4.3% | 24 |
| I | 10.00 | 10.08 ± 0.269 | 100.8% | 2.7% | 24 |
| J | 14.00 | 14.14 ± 0.424 | 101.0% | 3.0% | 24 |
| K | 18.00 | 17.61 ± 0.535 | 97.8% | 3.0% | 24 |
| L | 20.00 | 19.98 ± 0.580 | 99.9% | 2.9% | 24 |

TABLE 9

SUMMARY OF THE VERAPAMIL/NORVERAPAMIL ANALYTICAL METHOD

| | |
|---|---|
| Matrix | Plasma |
| Volume Required | 1.0 ml |
| Anticoagulant | EDTA |
| Extraction Cartridge | Cartridge IX |
| Concentration range | 2.00–500.93 ng/ml for Verapamil |
| | 2.06–514.76 ng/ml for Norverapamil |
| Chromatography | High resolution capillary |
| Detection Mode | NPD |
| Quantitation Method | Internal Standard Method |
| Quantitation by | Peak Height Ratio |
| Regression | Ln polynomial |
| Goodness of fit | The correlation coefficients were better than or equal to 0.9987 for Norverapamil/Verapamil |
| Verapamil Recovery | 79.4% at 5.03 ng/mL |
| | 82.0% at 201.11 ng/mL |
| | 80.1% at 402.22 ng/mL |
| Norverapamil Recovery | 80.6% at 5.24 ng/mL |
| | 86.5% at 209.59 ng/mL |
| | 91.0% at 419.19 ng/mL |
| Stability | Stable at room temperature in plasma for 8 hours |
| | Stable in plasma after three freeze-thaw cycles |
| | Stable in injection solvent for 15.5 hours |

TABLE 10

BETWEEN-RUN PRECISION AND ACCURACY FOR NORVERAPAMIL IN HUMAN PLASMA

| Samples | Nominal Value (pg/mL) | Mean ± SD (pg/mL) | Mean as % of Nominal | CV % | n |
|---|---|---|---|---|---|
| A | 2.06 | 2.01 ± 0.223 | 97.4% | 11.1% | 19 |
| B | 5.24 | 5.03 ± 0.542 | 95.9% | 10.8% | 20 |
| C | 209.59 | 209.00 ± 9.777 | 99.7% | 4.7% | 20 |
| D | 419.19 | 417.65 ± 20.471 | 99.6% | 4.9% | 20 |
| E | 2.06 | 2.34 ± 0.125 | 113.7% | 5.3% | 5 |
| F | 4.12 | 3.48 ± 0.164 | 84.6% | 4.7% | 5 |
| G | 10.30 | 10.15 ± 0.716 | 98.6% | 7.0% | 4 |
| H | 51.48 | 52.88 ± 2.762 | 102.7% | 5.2% | 5 |
| I | 102.95 | 109.01 ± 7.033 | 105.9% | 6.5% | 4 |
| J | 257.38 | 276.20 ± 29.383 | 107.3% | 10.6% | 4 |
| K | 463.28 | 419.40 ± 13.141 | 90.5% | 3.1% | 5 |
| L | 514.76 | 530.49 ± 21.214 | 103.1% | 4.0% | 5 |

TABLE 11

BETWEEN-RUN PRECISION AND ACCURACY FOR VERAPAMIL IN HUMAN PLASMA

| Samples | Nominal Value (pg/mL) | Mean ± SD (pg/mL) | Mean as % of Nominal | CV % | n |
|---|---|---|---|---|---|
| A | 2.00 | 1.81 ± 0.163 | 90.7% | 9.0% | 19 |
| B | 5.03 | 4.89 ± 0.479 | 97.2% | 9.8% | 20 |
| C | 201.11 | 202.33 ± 8.786 | 100.6% | 4.3% | 20 |
| D | 402.22 | 399.10 ± 16.536 | 99.2% | 4.1% | 20 |
| E | 2.00 | 2.11 ± 0.157 | 105.7% | 7.4% | 5 |
| F | 4.01 | 3.74 ± 0.263 | 93.2% | 7.0% | 5 |
| G | 10.02 | 10.24 ± 0.885 | 102.2% | 8.6% | 4 |
| H | 50.09 | 47.58 ± 2.008 | 95.0% | 4.2% | 5 |
| I | 100.19 | 105.06 ± 5.655 | 104.9% | 5.4% | 5 |
| J | 250.46 | 268.83 ± 16.403 | 107.3% | 6.1% | 5 |
| K | 450.83 | 434.13 ± 11.390 | 96.3% | 2.6% | 5 |
| L | 500.93 | 490.50 ± 13.163 | 97.9% | 2.7% | 5 |

TABLE 12

SUMMARY OF THE GLIPIZIDE ANALYTICAL METHOD

| | |
|---|---|
| Matrix | Plasma |
| Volume Required | 1.0 ml |
| Anticoagulant | EDTA |
| Extraction Cartridge | Cartridge III |
| Concentration range | 15.0–1000.0 ng/ml |
| Chromatography | High resolution capillary |
| Detection Mode | NPD |
| Quantitation Method | Internal Standard Method |
| Quantitation by Regression | Peak Height Ratio Log Polynomial |
| Goodness of fit | The correlation coefficients were better than or equal to 0.9950 |
| Recovery | 82.9% at 800.0 ng/mL |
| Stability | Stable at room temperature in plasma for 8.5 hours |
| | Stable in plasma after three freeze-thaw cycles |
| | Stable in injection solvent for 8 hours |

The chromatograms for each example show that the injected extracts are extremely clean, thus allowing relatively short run times for the GC which translates into high efficiency.

The extraction process according to the present invention is accurate at low levels of quantification and has good between run precision. Also, the process allows for fast extraction with resulting short processing times. The process further provides extracts with very low background contamination. Since there is so little background contamination, chromatography run times are drastically reduced from an average of 10–20 min per sample, for conventionally prepared samples, down to 3–5 min/sample. As an example, for the drug danazol, the average run time was reduced from greater than 20 minutes to about 3 minutes.

Additionally, the extraction process, according to the present invention, can be controlled by an experienced analyst when working with small numbers of samples. However, when working with typical bioanalytical batch sizes of 60–120 samples, it is difficult for the analyst to keep track of and adhere to the timing required for each addition of solvent for each cartridge. However, the process is well suited to automation, thereby resolving timing control, while permitting highly precise automated liquid handling and pipetting, and unattended extraction that frees the analyst for performing other work.

Figure 18:
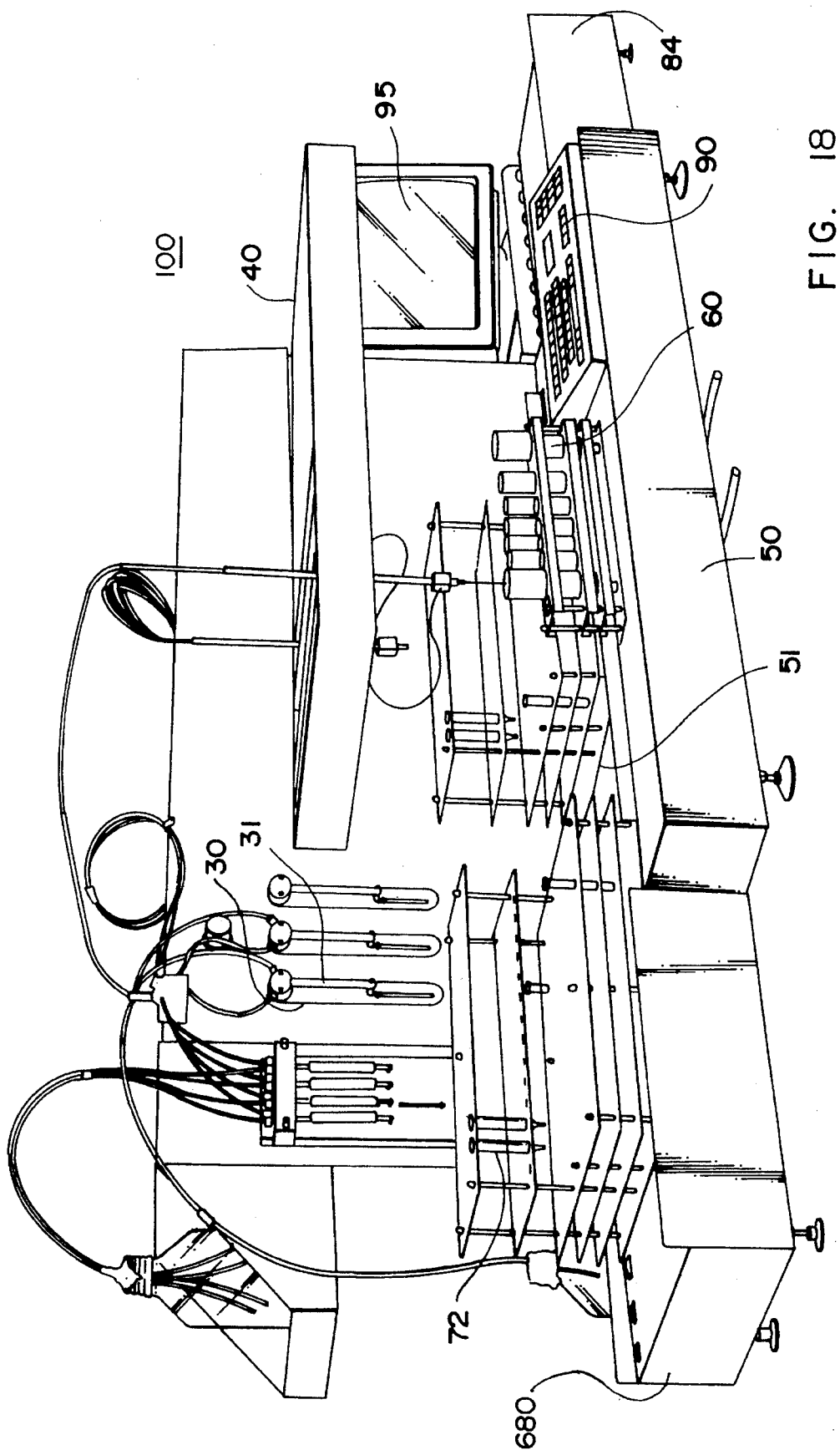
FIG. 18 is an elevated, perspective view of the processor system according to the present invention.

Accordingly, another aspect of the present invention is an automated processor system 100. As shown in FIG. 18, the processor system according to the present invention comprises an input extension unit 680, a main processing platform 50, an output extension unit 84, a robotic arm sampling system 40, a plurality of pumps 30, a plurality of syringe pumps 31, a wash station and internal standards rack 60, a keyboard 90 with a display 95. The automated processor system is shown in FIG. 8 with two racks 72 which hold the cartridges according to the present invention.

Figure 19:
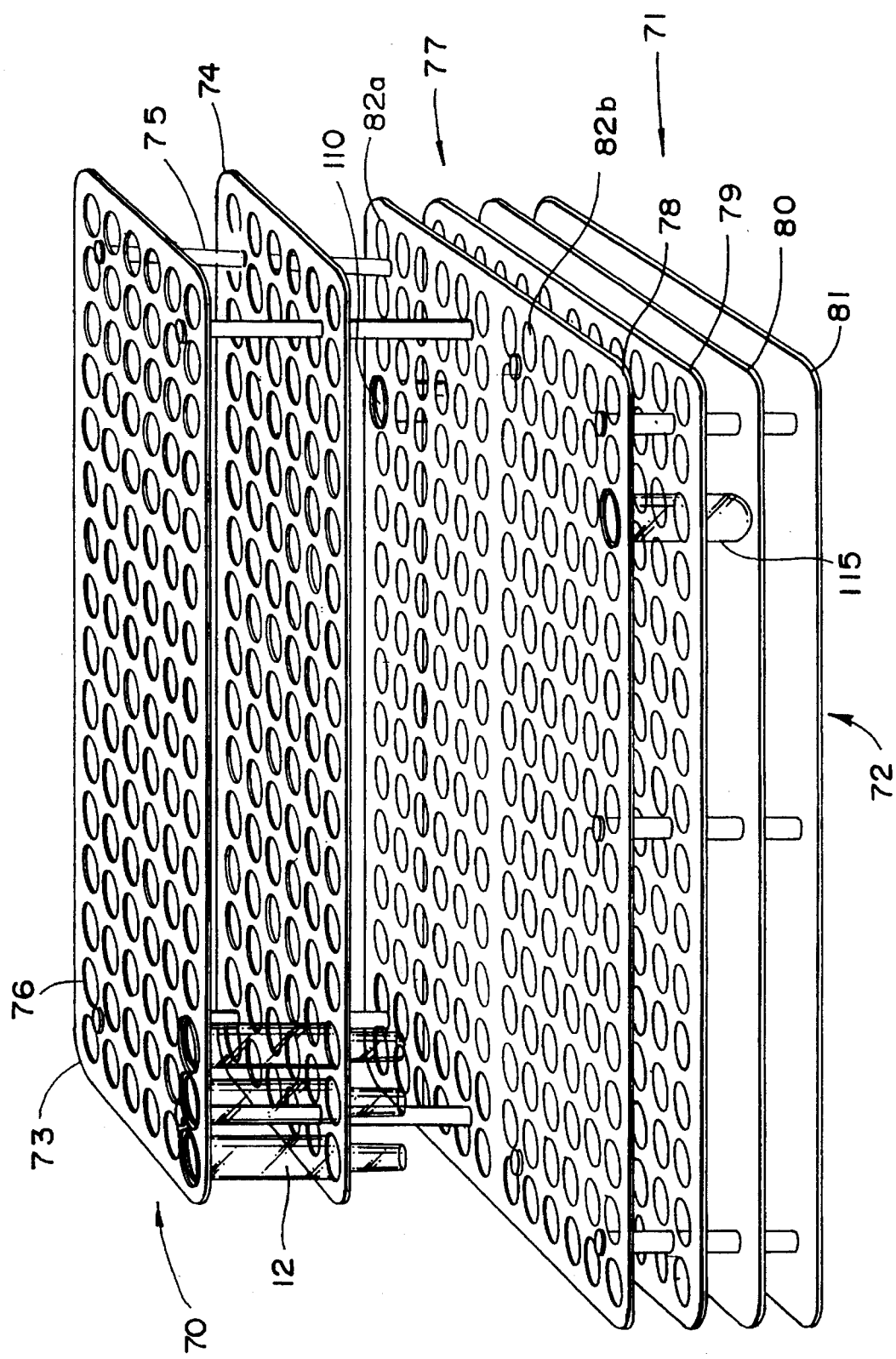
FIG. 19 is an elevated, perspective view of the rack according to the present invention.

As illustrated in FIG. 19, the rack 72 includes an upper rack 70 and a lower rack 71. The upper rack 70 comprises a plurality of plates, such as two plates 73, 74 which are connected by a plurality of posts 75. Each of plates 73, 74 contains a plurality of openings 76 into which cartridges 12 are placed. The openings are constructed and arranged so that the cartridges are held in the upper rack in a substantially vertical orientation.

The top rack 70 is fitted onto the lower rack 71 so that it is positioned over the back portion 77 of lower rack 71.

Lower rack 71 comprises a plurality of plates. Preferably, the lower rack 71 includes upper plate 78, middle plate 79 and lower plate 80. Each of the upper, middle and lower plates includes a plurality of openings 82a and 82b for holding collection tubes 110 and sample tubes 115, respectively. The openings 82a and 82b are constructed and arranged so that the collection and sample tubes are substantially vertically oriented. In particular, the collection tubes 110 are positioned in openings 82a in the back portion 77 of lower rack 71 underneath each of the cartridges 12 positioned in the upper rack 70 to collect the eluate that includes the extracted drug and solvent for a corresponding cartridge.

Figure 20:
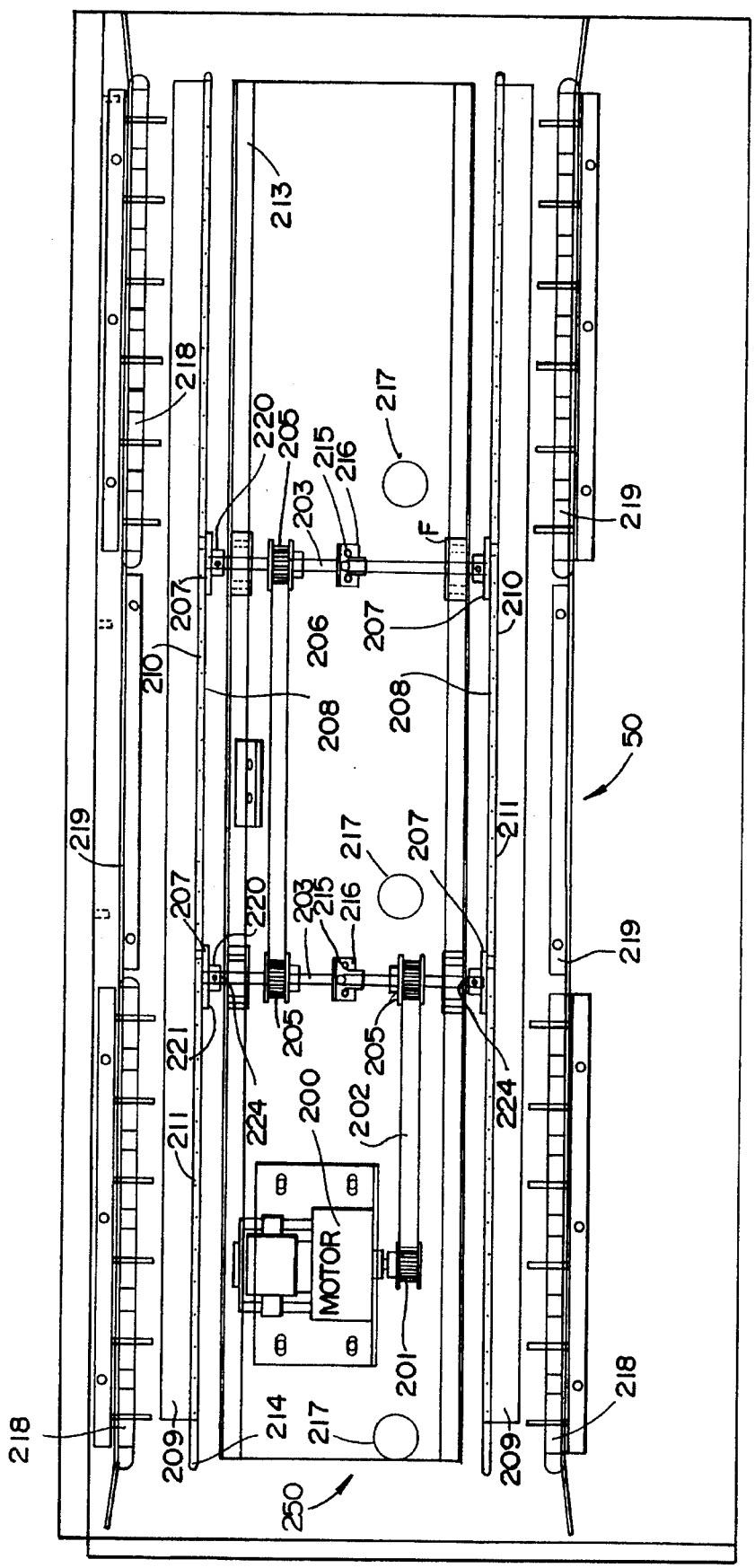
FIG. 20 is a bottom, cutaway view of the main processing platform according to the present invention.
Figure 21:
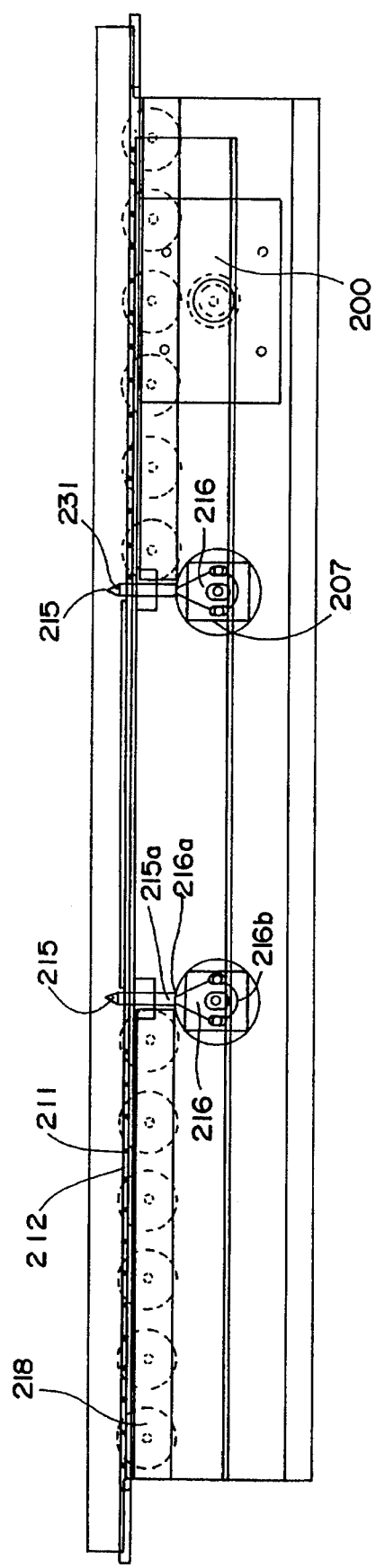
FIG. 21 is a front, cutaway view of the main processing platform according to the present invention.
Figure 22:
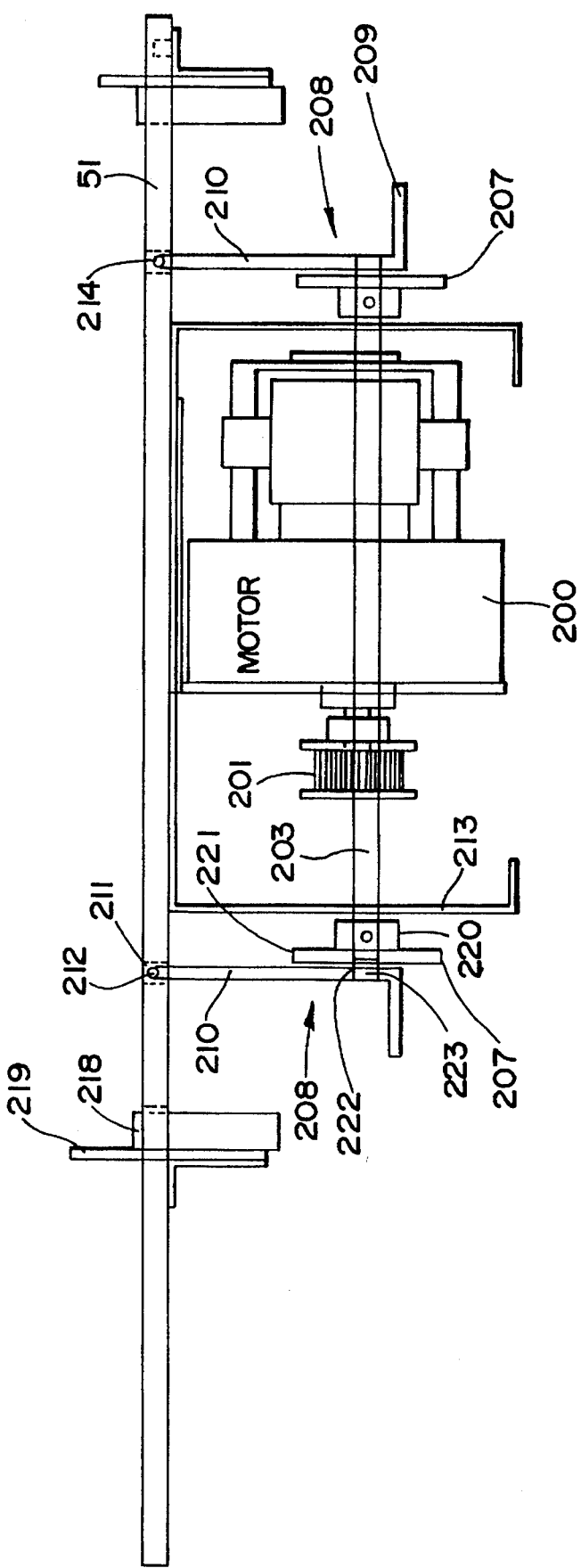
FIG. 22 is a side, cutaway view of the main processing platform according to the present invention.

Sample tubes 115, for holding the biological fluid containing the drug to be extracted, are positioned in the openings 82b in the front portion 78 of the lower rack 71. The lower rack 71 also comprises bottom plate 81, which, as will be described below, engages the top surface 212 of elongated member 208, which is shown in FIGS. 20–22, so that the elongated member can lift rack 72, move the rack forward and place the rack back down on the working surface 51. The upper rack 70 can hold any number of cartridges 12 with a corresponding number of collection tubes 110 placed below the cartridges. Preferably, the rack 72 is capable of holding ninety six of each of cartridges 12, collection tubes 110 and sample tubes 115, with the lower rack 71 having 12 columns and 16 rows of openings, and the upper rack 70 having 6 columns and 16 rows of openings. Preferably, the length of the rack is seventeen inches.

FIGS. 20–23 illustrate the main processing platform 50. As shown in FIG. 20, the main processing platform includes a walking beam 250 including a motor 200 that drives a pulley 201 attached to a belt 202, which in turn drives a plurality of shafts 203 using pulleys 205 and belt 206. Preferably, the motor operates at approximately 6 rpm. Positioned at each end 224 of shafts 203 are pulleys 207. Also positioned on shafts 203 are cams 216 onto which are mounted locking pins 215.

Both sides of the elongated member 208 are eccentrically mounted on pulleys 207. As shown in FIGS. 20 and 22, preferably two elongated members 208 are mounted on pulleys 207 at each of the ends 224 of shafts 203. As shown in FIG. 22, the elongated member 208 is preferably L shaped with substantially horizontal portion 209 being substantially perpendicular to substantially vertical portion 210. The top surface 212 of elongated member 208 engages the bottom surface 84 of bottom plate 81, as shown in FIG. 19a, to lift the rack 72, move it forward and set it back down on the working platform 51.

The top surface 212 of elongated member 208 and the bottom surface 84 of the rack 72 can be constructed and arranged in any manner that enables the rack to be lifted and moved forward. In particular, while the top surface 212 of the elongated member 208 and the bottom surface 84 of the rack 72 can be constructed with smooth surfaces, it is preferred that at least one of the surfaces include a construction so as to increase friction between the elongated member and the rack. For example, the top surface 212 can include a plurality of protrusions 211 thereon, positioned so as to contact the bottom surface 84 of the rack. Also, the bottom surface 84 of the rack can include openings 411 or recesses 412 corresponding to the protrusions 211, which are illustrated in FIG. 19a. The protrusions and openings can be reversed, so that the protrusions are located on the bottom surface 84 of the rack; however, it is preferred that the protrusions be on the elongated member.

Further, at least one of the top surface 212 or the bottom surface 84 of the rack can be roughened, such as partially illustrated at 410, or include a high friction surface, such as a rubberized surface, to increase the friction therebetween.

Figure 19A:
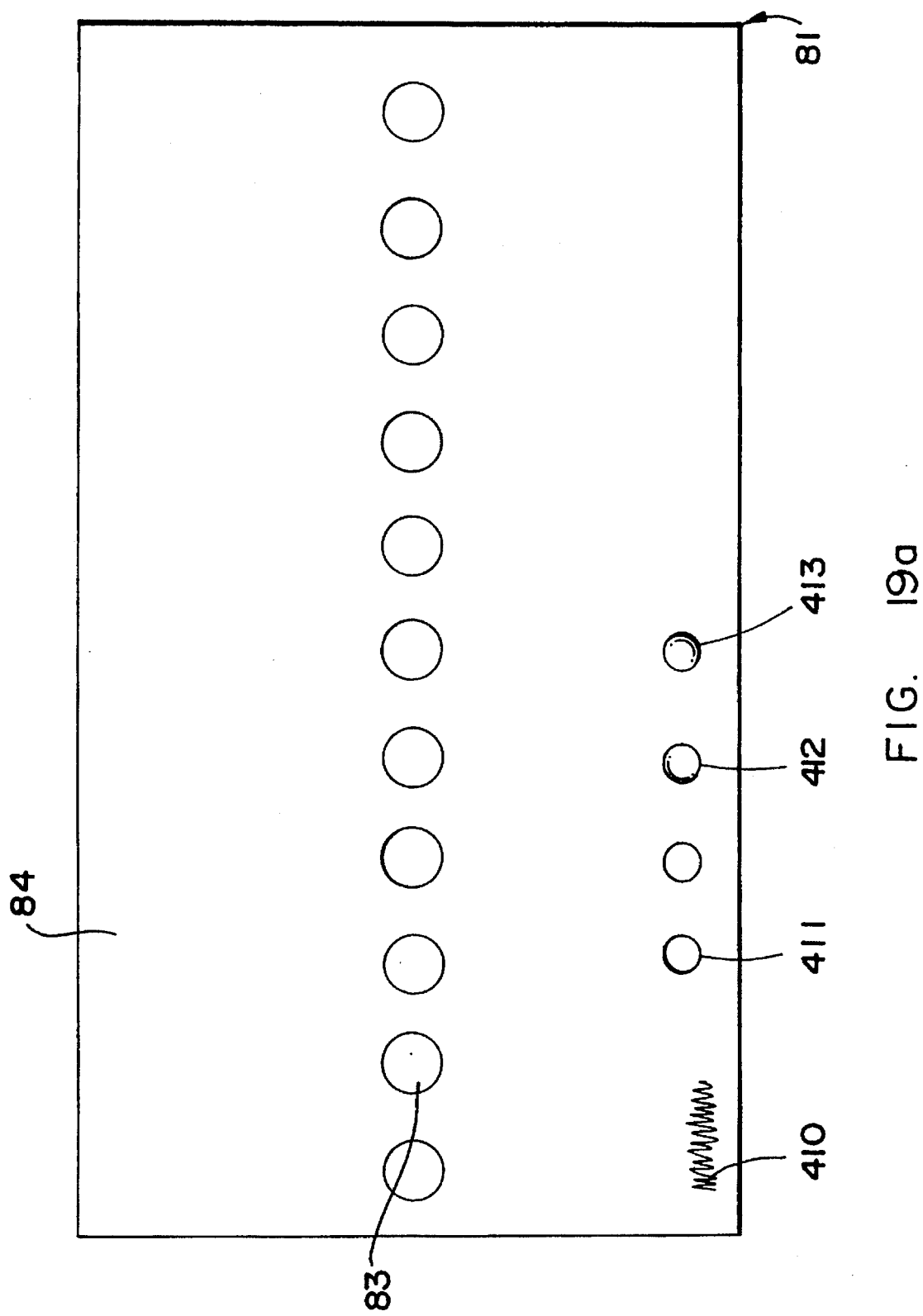
FIG. 19a is a bottom view of the bottom plate of the rack according to the present invention.

As shown in FIG. 19A, the bottom plate 81 includes a plurality of locking openings 83. The locking openings 83 are dimensioned to receive pins 215 of elongated member 208, shown in FIG. 20, so as to hold a rack 72 in a set position. In other words, the pins 215 and the locking openings 83 cooperate to maintain the rack in indexed positions, as the rack is moved row-by-row along the working surface 51. Preferably, the bottom plate 81 includes fifteen locking openings 83 equally spaced one inch apart.

Figure 23:
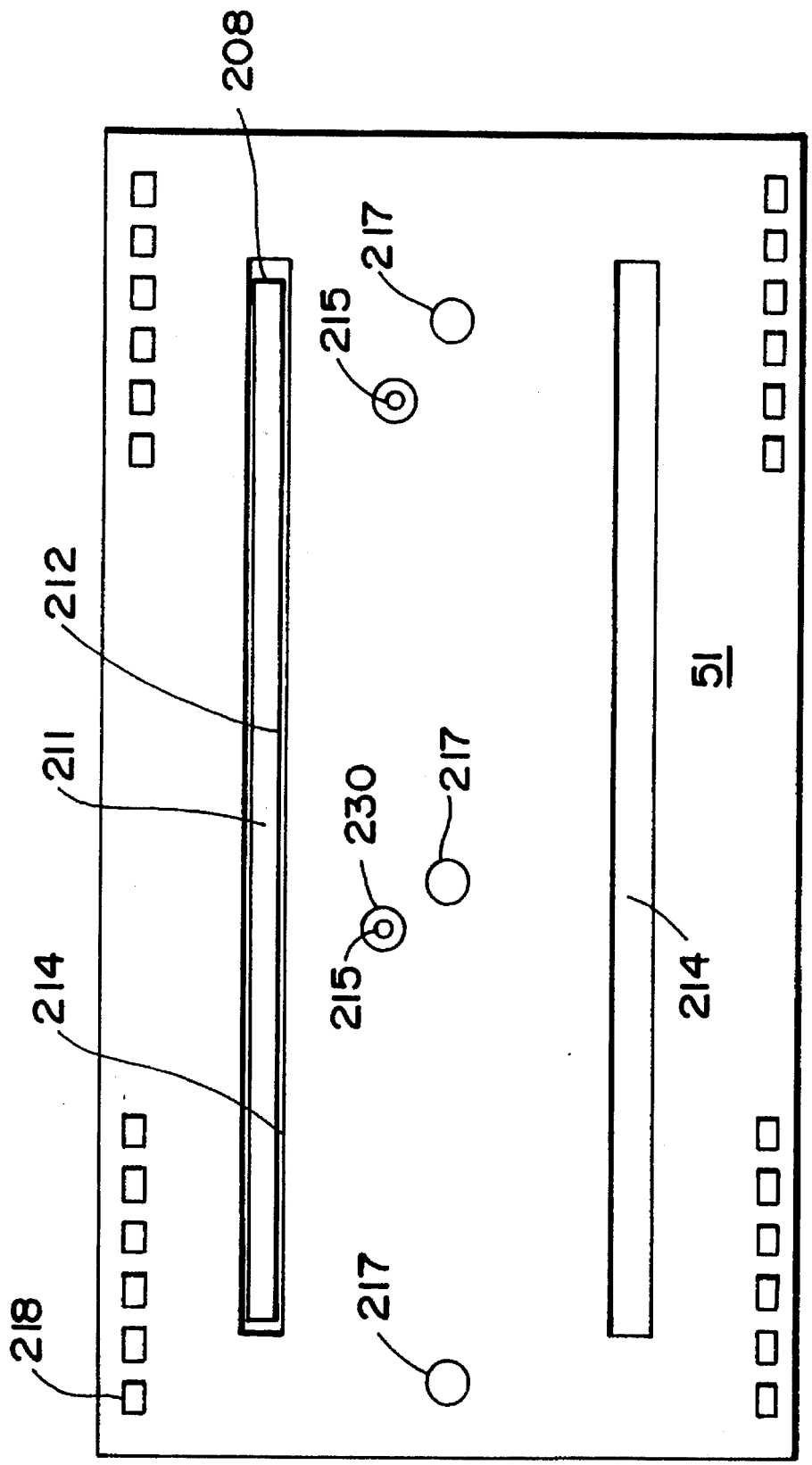
FIG. 23 is a top view of the main processing platform according to the present invention.

As shown in FIG. 23, each elongated member 208 is positioned under slot 214 in the working surface 51. The walking beam 250 moves the rack 72 a precise, predetermined amount along the working surface 51 by turning one revolution, i.e, the motor 200 and the attached pulleys, belts, shafts and elongated members move in one revolution increments. Each revolution moves the rack 72 a predetermined amount and thereby moves another row of cartridges 12, collection tubes 110 and samples tubes 115 toward and underneath the robotic sampling system 40 to position another row of cartridges for receiving a sample to be extracted therein.

The locking pins 215, which are preferably about 0.25 inch in diameter, can include an upper portion 231, are raised above the working surface 51 through apertures 230 to engage the locking openings 83 of FIG. 19a of the rack to lock the rack in position. The locking pin 215 is constructed and arranged to protrude through the working surface 51 to the extent necessary to cooperate with locking openings 83 to maintain the rack 72 in a set, indexed position. For example, the locking pin 215 can protrude into the locking opening 83 or can go through the opening. In a preferred embodiment, locking pin 215, protrudes 0.75 inches above the working surface.

The locking pin 215 is constructed so that it is capable of setting the position of the rack at the end of one revolution of the walking beam. The upper portion 231 of locking pin 215 protruding above the surface of the working area 51 is constructed and arranged to ensure that the locking pin fits tightly into the locking opening 83, and also smoothly releases the rack before the next forward movement takes place. Furthermore, the upper portion 231 of locking pin 215 should have a preferred profile to be capable of correcting small misalignments of the rack without jarring or jamming the rack. For example, upper portion 231 preferably has a tapered shape to provide ease of insertion and release, with precise positioning of the rack.

The height of locking pin 215 and the shape of cam 216 determines the height of the locking pin with respect to the working surface 51. In this regard, cam 216 can have a pear-shaped structure so that, as shaft 203 rotates, portion 216a and 216b alternatively come into contact with lower end 215a of locking pin 215. When portion 216a is in contact with the lower end 215a, the locking pin is in its raised position and when portion 216b is in contact with the lower end 215a, the locking pin is in its lowered position.

The operation of the walking beam to advance the rack by one increment is described as follows. At the beginning of a revolution, the elongated members 208 are positioned below the working surface 51 and locking pin 215 is positioned above the working surface 51 in a locking opening 83. As the shafts 203 start to rotate, locking pin 215 moves down, and, at the same time, the elongated members 208 move up above the working surface 51 through slots 214 so that the upper surface 212 engages the bottom surface 84 of rack 72. As the shafts 203 continue to rotate, the elongated members 208 raise rack 72 and move the rack 72 forward a precise, predetermined amount, i.e, one increment. As the revolution of shafts 203 continues, the elongated members 208 lower rack 72 back down onto working surface 51, returning through slots 214 below working surface 51 and the locking pin 215 moves up to lock the rack in the new position by entering a locking opening 83. At this time, rotation is stopped, and the revolution for moving one increment is complete.

The dimensions of the elongated members, the pulleys and the location of the elongated members on the pulley determine the distance the rack is moved with each revolution. Preferably, the elongated members are approximately 41 inches long and 2.5 inches in height. If two elongated members are used they are preferably spaced apart approximately 7.25 inches.

Further, the pulleys 207 preferably include a larger portion 221, approximately 2.25 inches in diameter, onto which the walking beam is mounted and a smaller portion 220 approximately 1.5 inches in diameter. A hole 222, preferably 0.25 inches in diameter is located approximately 1.875 inches below the top surface 212 of the elongated member for attaching pulley 207 by attachment means 223. The attachment means can be any attachment means known in the art such as screws, bolt and nut or welding. The specific dimensions cited above will result in a movement of the rack of approximately one inch when the walking beam completes one revolution. These dimensions can be varied depending on the amount of movement desired.

Also included in the working surface 51 is a plurality of proximity sensors 217, that sense the position of the rack on the working surface. The proximity sensor can be any position sensor known in the art. For example, the sensor can be a mechanical switch positioned above the working surface 51 that is pushed down by the rack as it reaches the position of the sensor thereby indicating the position of the rack and to thereby control stopping of the revolution. The sensor can also be a photoelectric sensor that is capable of detecting one revolution of the walking beam and automatically stopping the walking beam. This photoelectric sensor includes a wheel with a 0.25 inch diameter opening which allows a light beam to strike the photocell at a predetermined position in the walking beam cycle. A preferred sensor is an electromagnetic proximity detector available from TURCK Inc., Minneapolis, Minn.

As shown in FIG. 22, the motor 200 as well as the components associated therewith are preferably mounted to the lower surface of the working surface 51 by frame 213 using any attachment means known in the art. For example, the motor can be attached using screw, nuts and bolts, or welding.

The main processing platform can also include a plurality of idlers 218 positioned in the working surface for supporting the rack. Preferably, idlers 218 are approximately 1.5 inches in diameter. The rack 72 is guided on the working surface 51 of the main processing platform 50 by two parallel angles 219. The idlers are attached to the platform using any attachment means known in the art.

Figure 24:
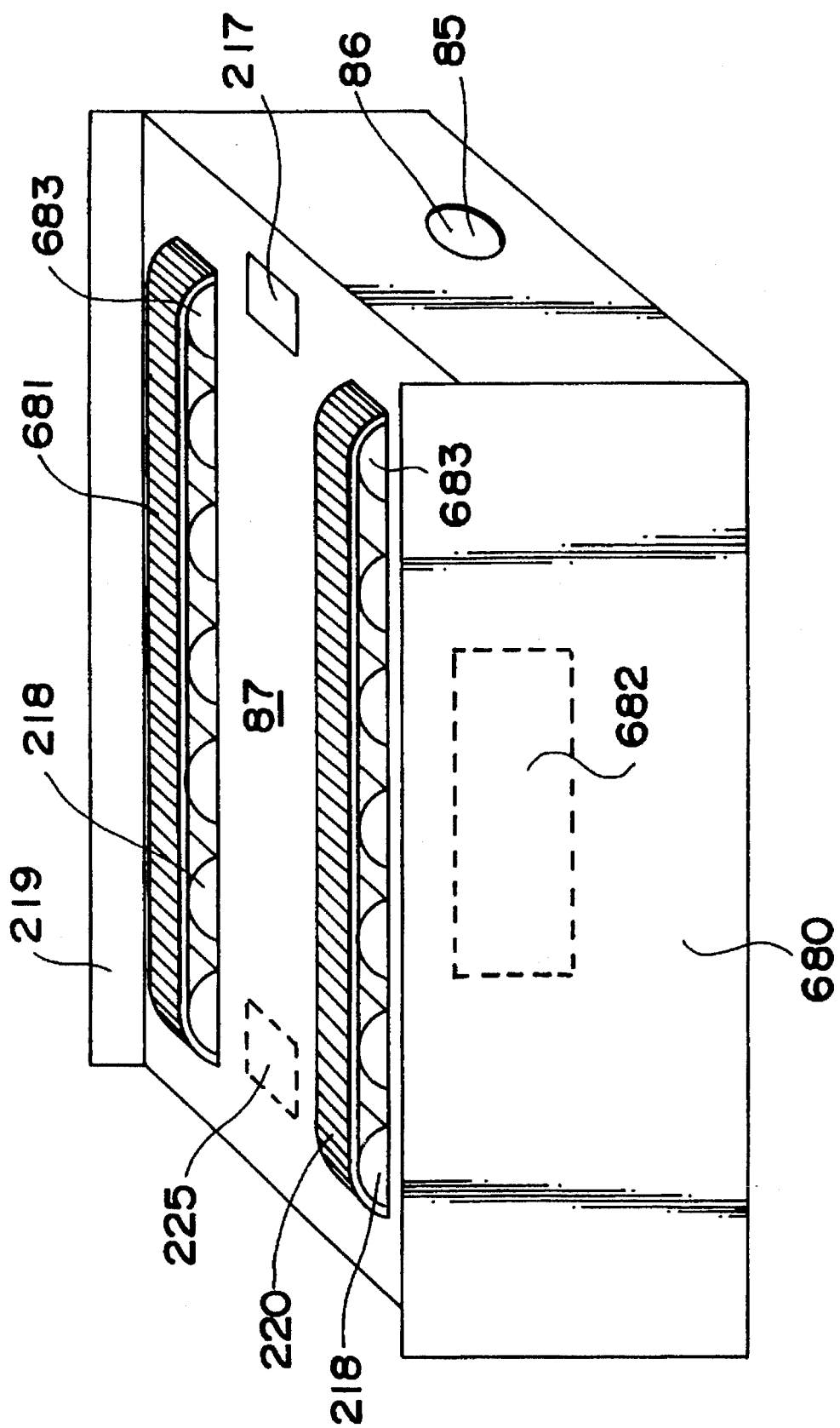
FIG. 24 is an elevated, perspective view, with the top partially cut way, of the input extension unit according to the present invention.

More specifically, the processor system according to the present invention can also include an input extension unit 680 for automatically feeding a rack 72 onto the main processing platform 50, and an output extension unit 84 for removing the processed rack from the processor system. As shown in FIG. 24, the input extension unit 680 includes a conveyor belt 681 and a geared down 12 rpm drive motor

682 that drives the belt through pulleys 683. The unit also contains a proximity sensor 217 to sense the rack position. The power and control signals are connected to the computer the main unit by two separate connectors 85, 86. Similar to the main processing platform 50, the input extension unit 680 can also include a plurality of idlers 218 positioned within the surface 87 over which passes the rubber conveyor belt 681. The rack is placed on the rubber conveyor belt 681, which is preferably a rubber timing belt. The rubber timing belt provides enough friction to drive the rack onto the main processing platform. Preferably, idlers 218 are approximately 1.5 inches in diameter. The rack 72 is guided on the input extension unit 680 by two parallel angles 219. The input extension unit is positioned against the main processing platform with proximity detector 217 positioned toward the main processing platform.

The output extension unit 84 is preferably substantially identical to the input extension unit, and so as not to be unduly duplicative, the output extension unit is not illustrated in the drawings. In this regard, any discussion and/or illustration of the input extension unit can also be considered to be a discussion and/or illustration of the output extension unit. The output extension unit is positioned with the proximity sensor 225 away from the main processing unit.

The plurality of syringe pumps 30, 31 used in the present invention can be any commercially available liquid pumps known in the art. All actions of the syringe pumps and the movement of the automatic sample processor are controlled by a computer system, which will be described below. The computer system links the two syringe pumps and the movement of the automatic sample processor to allow the complete extraction process to be executed continuously and repeatedly.

As noted above, the process of extraction involves the transfer of precise volumes of liquid. For example, the extraction process begins with the transfer of an internal standard, preferably 0.1 ml, from an internal standard reservoir 63 to each cartridge in a row of six. This is followed by the transfer of 1.0 ml of sample from a sample tube to the corresponding cartridge in that row and finally the addition of 5 or 6 volumes of about 1.5 ml of a solvent or solvent mixture to each cartridge at predetermined time intervals.

The transfer of precise volumes of liquid is accomplished using a number of highly specialized syringe pumps. This type of pump is capable of delivering accurate, reproducible amounts of liquid and it can both aspirate and dispense. It is also readily adaptable to different volume requirements, i.e., 50 microliters to 25 ml per full stroke, by simply changing the size of the syringe. Furthermore, the volume dispensed or aspirated is only little affected by the type or viscosity of the liquid to be pumped. This type of pump consists of an accurate stepper motor which moves the plunger in the calibrated syringe barrel at controlled speeds over defined distances resulting in aspiration or dispensing of an accurate volume of liquid. Examples of commercially available syringe pumps that are useful in the present invention are manufactured by Cavro ( Cavro Scientific Instruments, Inc., Sunnyvale, Calif. 94089).

Specifically, two Cavro type XL3000 modular, single channel pumps (type 724024) are used to transfer the sample, water for washing and internal standard. These two pumps are connected by flexible plastic tubing, preferably PTFE or PFA, to the sample probe 48 held in z-rack 46 of Arm I 41*a* of the robotic sample processor 40, shown in FIG. 25*a*. One of the single channel pumps is equipped with a syringe of 1 ml capacity, and performs all aliquoting steps involving samples and internal standards. The other single channel pump has a capacity of 10 ml, and provides water for the washing process required between any two dissimilar samples handled consecutively by the probe 48.

Figure 26A:
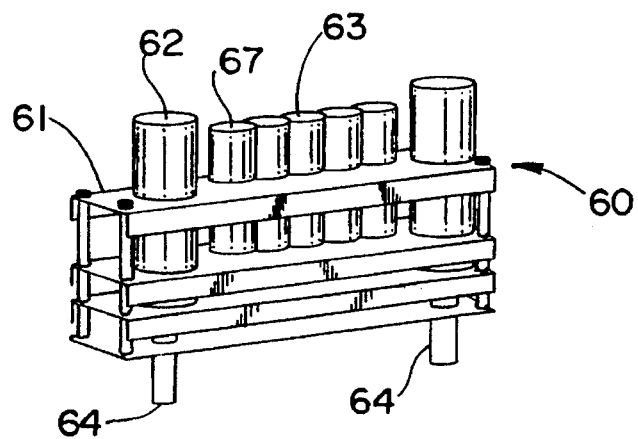
FIG. 26a is a side view of the wash station according to the present invention.
Figure 26B:
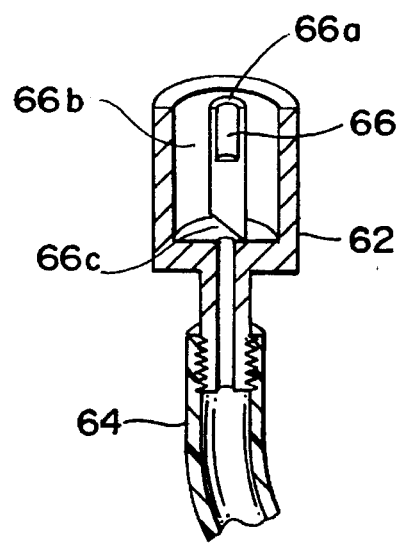
FIG. 26b is a cut away view of a washing reservoir according to the present invention.

As shown in FIG. 26*a*, washing is done in the wash station 62. The rack 61 is mounted on the working platform just next to the walking beam but is still accessible by the robotic arms. A cut-away view of the wash station is shown in FIG. 26*b*. During washing the probe 48 is placed in cavity 66 having a preferred depth of about 1 inch, and approximately 5–10 ml of water ml is pumped through probe 48 to wash both the inside and outside of the probe 48. As the wash fluid is pumped into the cavity 66, the wash fluid overflows over the top edge 66*a* of the cavity 66 into the annular chamber 66*b* and down through opening 66*c* into tube 64. In this regard, the probe should be inserted into cavity 66 at least to the depth that the probe is inserted into the sample or solvent to ensure proper washing action of the external surface of the probe. Reservoir 67 contains reagent water, such as deionized water, to be used in the process. The rack includes a plurality of internal standard reservoirs 63.

The elution solvent is handled by a four-channel syringe pump which consists of four syringes driven by the same stepper motor. A commercially available four-channel pump is the Cavro XL3004, type 724510. Each syringe dispenses and aspirates through a three-way solenoid valve. This allows the choice of one of four solvents to be delivered to any cartridge. The four syringes are connected to one of the four stainless steel dispensing probes 49 in the z-rack 46 of ARM II 41*b*, which are shown in FIG. 25*b*, by four independent plastic tubes (preferably PTFE) 44. The probes are held in place in the z-rack 46 by two plastic inserts 500 at either end of the rack. These inserts have four holes through which the probes 49 pass. The probes can be made of Type 304W stainless steel tubing with an outer diameter (O.D.) of 0.058 inches to 0.120 inches and corresponding internal diameter (I.D.) of 0.042 inches and 0.094 inches; preferably with an O.D. of 0.083 inches and I.D. of 0.063 inches. This arrangement allows consecutive dispensing of different solvents without the need of washing the probe and plastic tubing between operations. This leads to a reduction in processing time, a crucial consideration for high speed equipment.

Figure 25A:
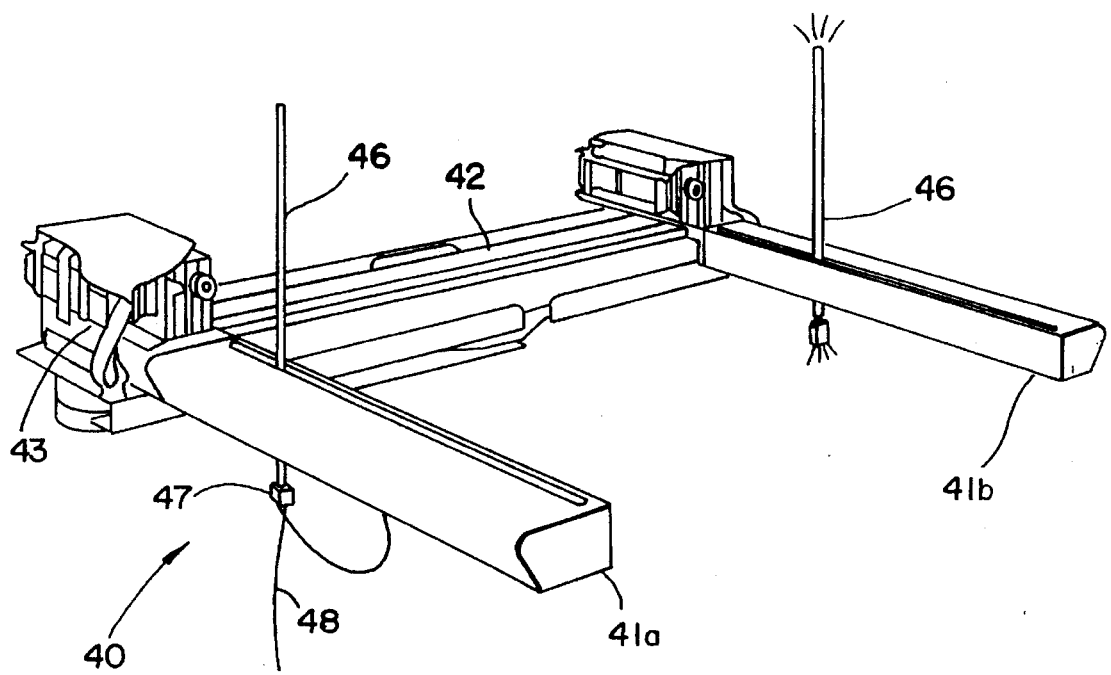
FIG. 25a is an elevated, perspective view of the robotic arm according to the present invention.
Figure 25B:
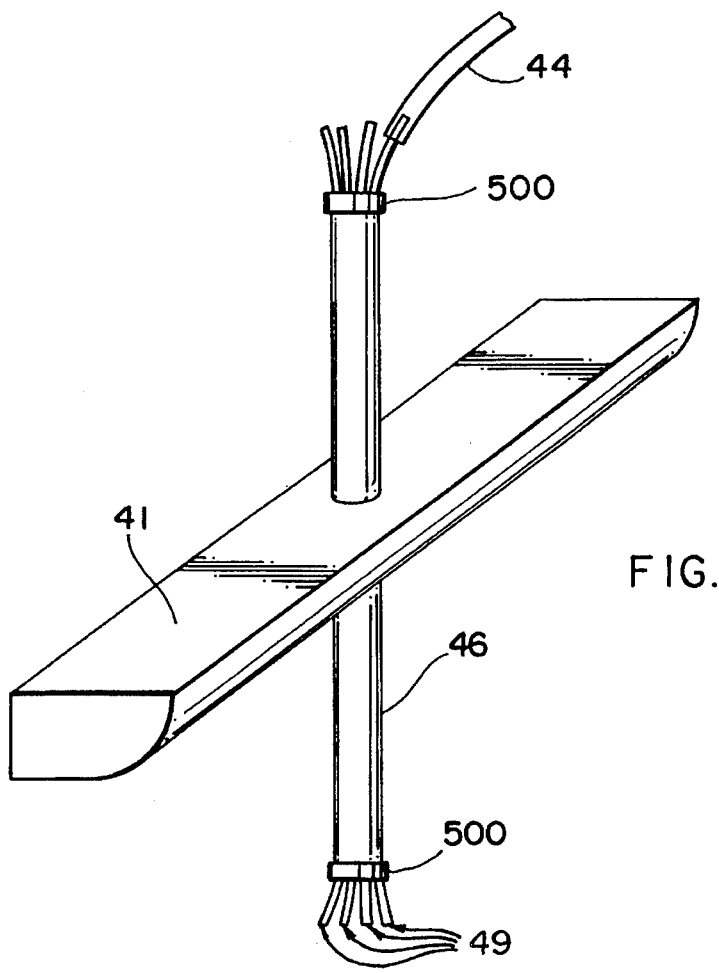
FIG. 25b is an elevated perspective view of the Z-rack of the robotic a arm according to the present invention.

The twin arm robotic sample processor 40, FIG. 25*a*, is a highly sophisticated handling system with mobility in the X, Y and Z directions. It can be directed through its own computer system to position the probes 48 and 45 at any position within its working span with extremely high accuracy. Appropriate equipment is supplied by Cavro Scientific Instruments, Inc., Sunnyvale, Calif., 94089. In particular their model RSP9652 is used for this invention. This model has an accuracy over travel of ±0.02 mm along the X axis, ±0.015 mm along the Y axis, and ±0.015 mm along the Z axis. This processor consists of two independently movable arms 41*a* and 41*b* mounted on the X-frame 42 by X-slide 43. Each arm 41*a* and 41*b* carries a Z-rack 46 which moves up and down (Z direction) and backwards and forwards (Y direction). To this is attached a sample probe 48 and an insulation block 47 which ensures that probe 48 is not electrically connected to the Z rack. This allows the probe to detect the level of a conductive liquid through a capacitance device supplied with the processor 40. If the probe finds either no sample or not enough sample in any sample tube, an error message is generated and no further processing of that sample tube and the corresponding extraction cartridge takes place. Further, the robotic arm is equipped with a self-diagnostic routine that sets the position of the probes when the apparatus is turned on.

Figure 27:
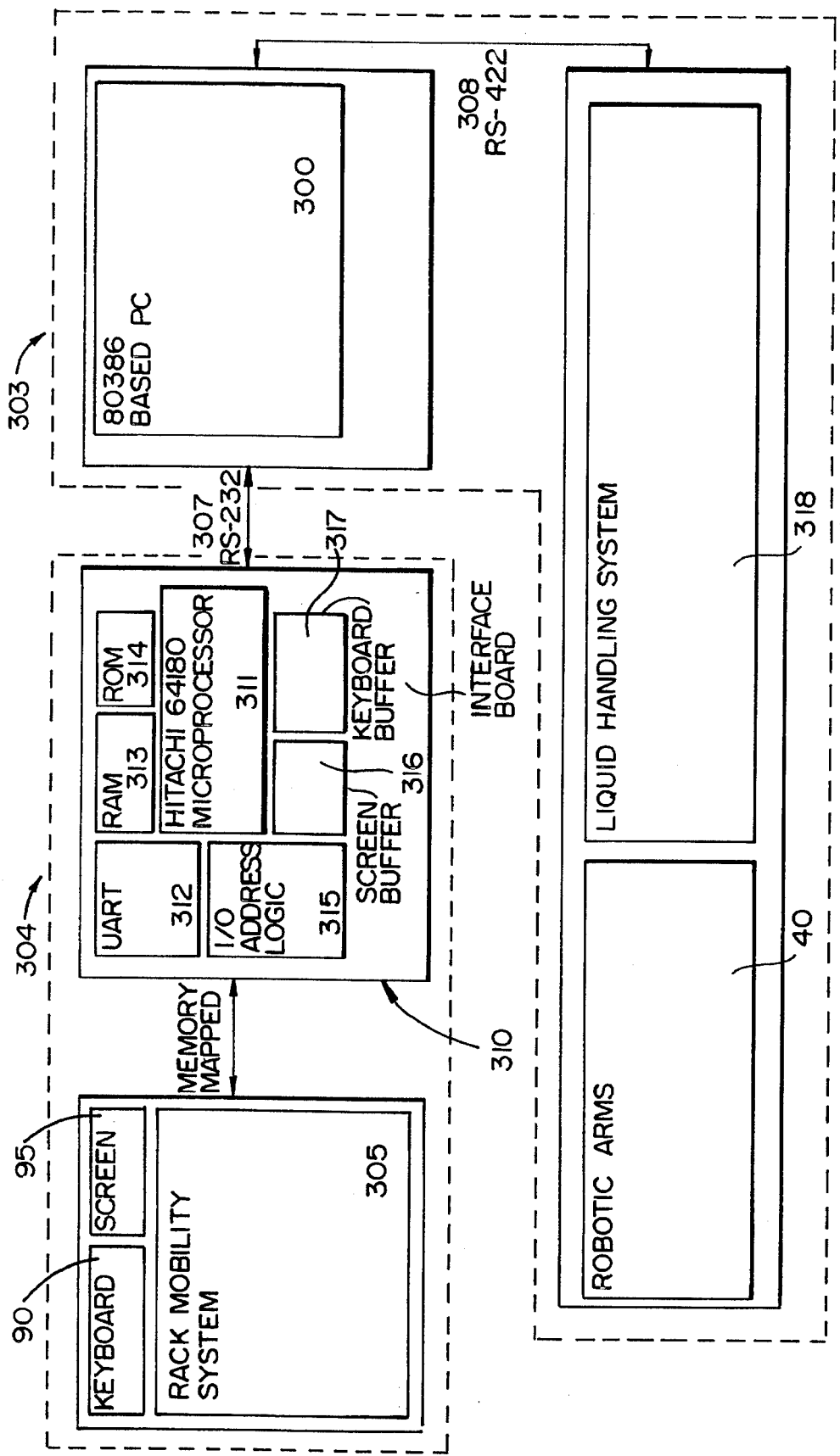
FIG. 27 is a block diagram of the computer hardware system according to the present invention.

Still another aspect of the present invention is the control of the processing system. The control of the processing system can be performed by a software-controlled computer system. In accordance with a particular embodiment of the present invention, the computer system comprises a dual-microprocessor system. The schematic chart in FIG. 27, illustrates an example of an embodiment of the hardware of the computer system according to the present invention. The system is divided into a master system 303, including master microprocessor 300, which directly controls the operation of the robotic arm sampling system 40 and the liquid handling system 318, which includes a plurality of syringe pumps 30, 31, and a slave sub-system 304, including interface board 310, which controls the operation of the keyboard 90, display 95 and rack mobility system 305. The rack mobility system 305 includes the motor 200, elongated members 208 and proximity sensors 217 of the main processing platform 51, as well as the motor 82, conveyor 81 and proximity sensor 217 of the input and output extension units 680, 84.

The master system can be implemented using any known personal computer including any known microprocessor, such as an IBM compatible PC. The slave sub-system may be implemented using any microprocessor known in the art, such as an 8-bit microprocessor. As shown in FIG. 27, master system 303 may be implemented with a personal computer having a 80386 class microprocessor 300. The 80386 microprocessor is directed through software to control the operation of the robotic arms 40 and the liquid handling system 30, 31. Commands are transmitted and received between the master system and the robotic arms and liquid handling system using standard RS-422 communications protocol; these commands are available from CAVRO Inc.

As show in FIG. 27, the slave sub-system 304 comprises an interface board 310 including a microprocessor 311. The illustrated board corresponds to a board produced by Chip Microsystems (Part No. PCB 1500) and includes a Hitachi 64180 microprocessor, which, as noted above, controls the operation of three devices: a keyboard 90, display 95, and a rack mobility system 305.

The slave sub-system microprocessor 311 may be configured so that is not multi-tasked, but rather is fully dedicated to monitor its serial interface for commands issued by the master. As each such command is received, sub-system microprocessor parses and executes the command in turn. Once each command is executed, a two character value is returned to the master to indicate the outcome of the execution. The master, in turns, takes an appropriate course of action.

The display 95 can comprise any known display capable of displaying alphanumeric information, e.g., being input by keyboard 90. By way of example, the display can comprise a 4×20 LED display with full buffering support. It displays system information, and messages, and serves as the keyboard's visual verification unit.

The keyboard 90 may comprise any keyboard capable of inputting the alphanumeric information needed to specify all needed information. By way of example, the keyboard can comprise a 64-key ASCII, non-repetitive unit. The slave sub-system 304 should be configured to provide a buffer 315 with the capacity of 2048 characters or more for the keyboard.

The two microprocessors communicate with each other using a standard RS-232 (307) communication protocol, via a suitable channel running at 9600 Baud or faster.

In addition to the microprocessor 311, the interface board 310 also includes a universal asynchronous receiver transmitter or UART 312 to implement the RS-232 protocol. Further, the interface board includes RAM 313 and ROM 314. The keyboard, screen, and rack mobility system are all memory mapped. That is, a region of memory is assigned to each of these devices so data can be accessed at these assigned memory addresses. The memory mapping is implemented in part by input/output address logic 315. The interface board also includes a screen buffer 316 and a keyboard buffer 317 each of which is reserved within RAM 313, for storing data that is sent to and from the screen and keyboard respectively.

Figure 28:
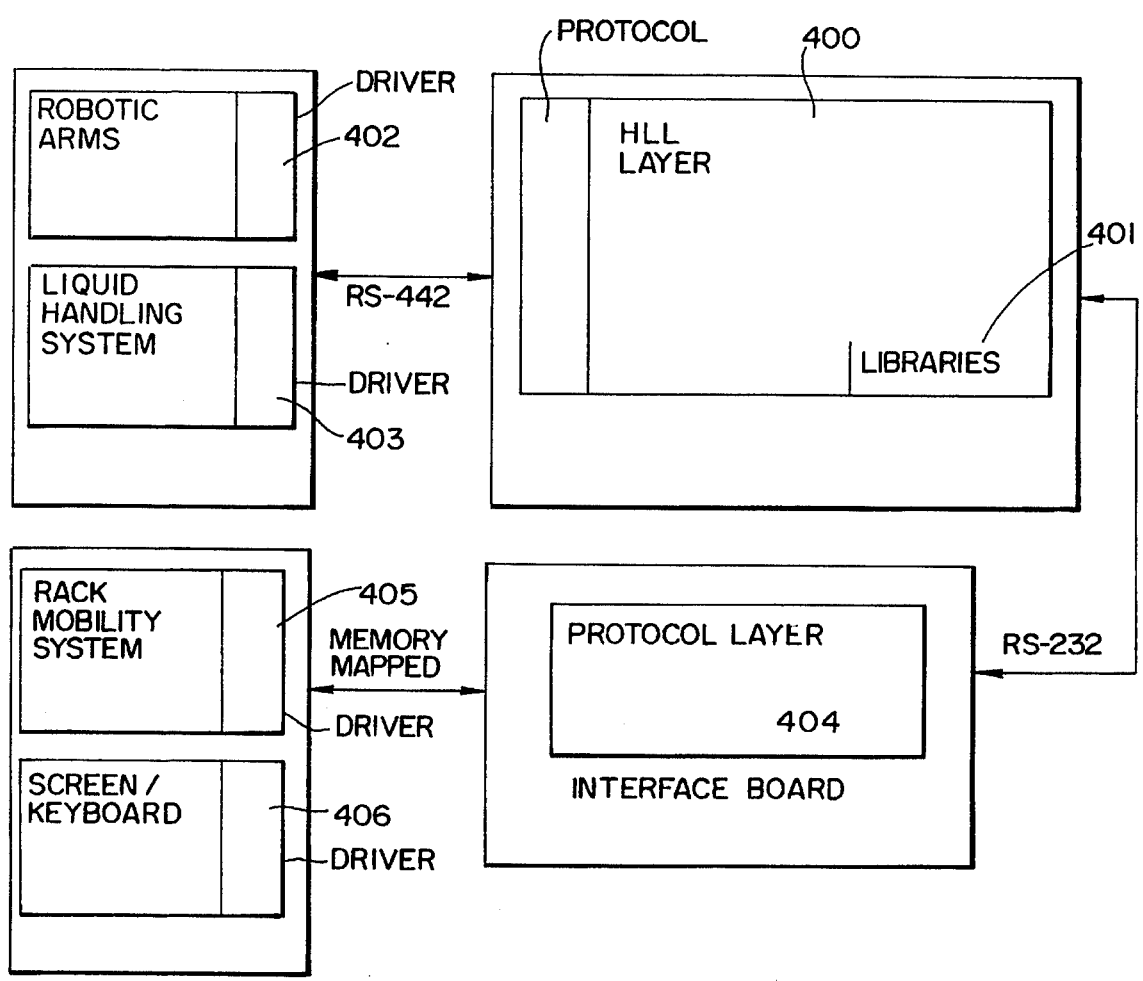
FIG. 28 is a block diagram of the software used in the computer control system according to the present invention.

FIG. 28 is a block diagram of the software used to operate the computer control system according to the present invention. The software 400 that operates on the master microprocessor is written in a High Level Language (HLL) that uses a Pascal-like syntax and encourages structured programming. The programming environment is available from CAVRO Inc., the manufacturer of a robotic sampling system useful in the present invention. The programming environment includes a library 401 comprising about 150 functions divided into 10 groups that allow the software engineer to issue commands to the above mentioned subsystems. The software also provides means of communicating with the outside world through its I/O library functions using the system's serial communication port. It is through this serial channel that the master system establishes a link with the interface board of the slave sub-system.

Drivers 402, 403 actuate the arms and pumps, respectively, in response to commands sent by the master system. The drivers 402, 403 are commercially available drivers that are provided with commercially available robotic arms and pumps. The preferred drivers are part of the robotic arms and pumps supplied by Cavro Scientific Instruments, Inc., as previously described.

As noted above, the HLL software that controls the function of the master microprocessor communicates with the interface board by standard communications protocol, for example RS-232. As shown in FIG. 28, the interface board controls the rack mobility system, the keyboard, and the screen using a string command based protocol 404.

The rack mobility system, the keyboard and the screen all respond to commands sent by the slave sub-system to their respective drivers, 405, 406. An example of the drivers useful for controlling the rack mobility system, the keyboard and the screen are available from Chip Microsystems.

The software controls the operation of numerous functions. For example, the software controls the execution of the extraction process, known as the production run, which is capable of processing one rack or multiple racks; it also controls the development of additional extraction methods, known as the method development run. Furthermore, a number of utilities are available which include automatic back-up, reprinting of run reports, network support for remote installation and debugging and calibration of the liquid handling system. The calibration program, production program and method development program will be described in detail below.

Calibration Program

Figure 29:
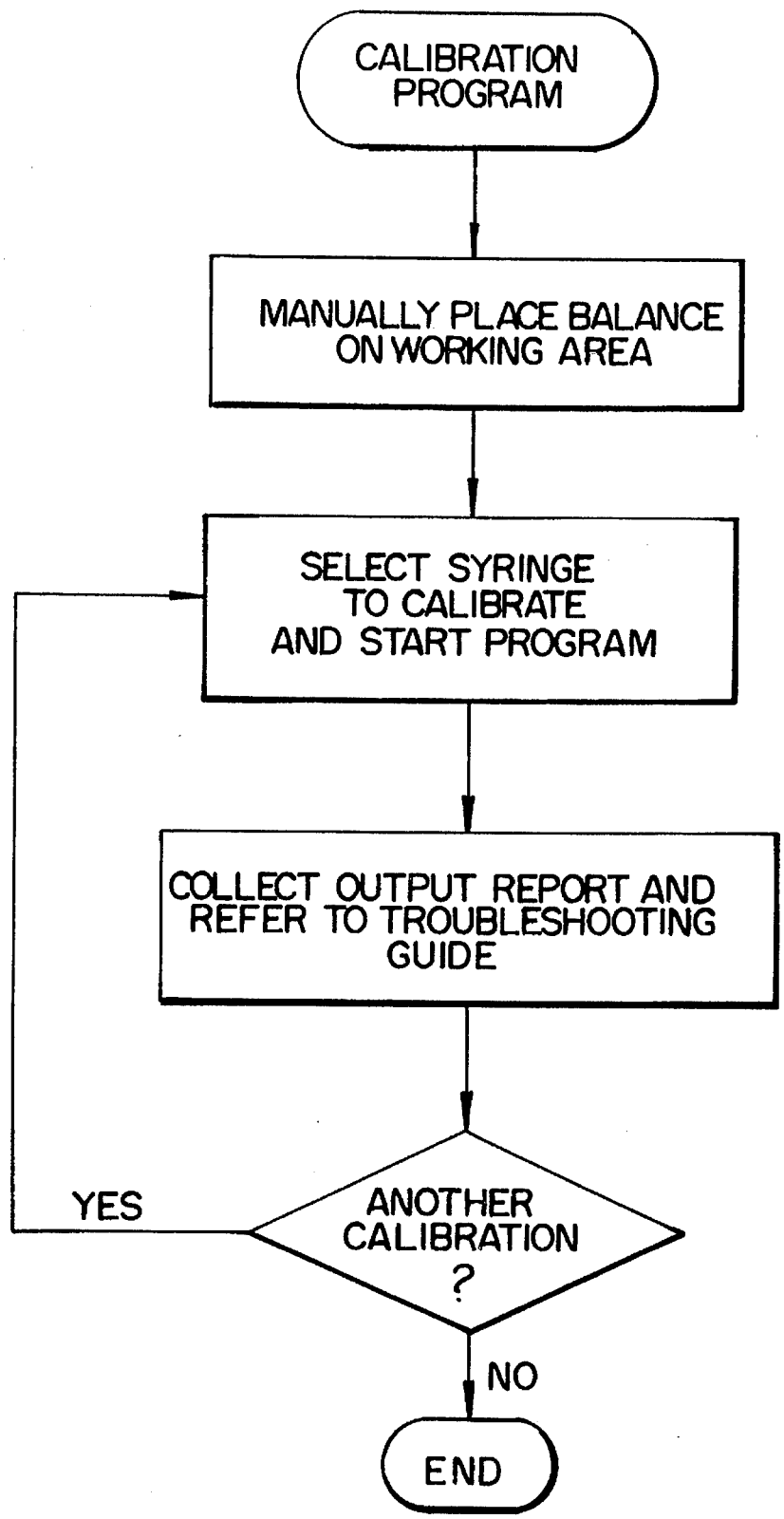
FIG. 29 is a flow chart of the calibration program according to the present invention.

Prior to using the automatic processing system, it is preferred that the system be calibrated to assure accurate delivery of samples, internal standards and solvents by measuring the amount of liquid that is delivered by each of the syringes in the robotic sampling system. The schematic diagram shown in FIG. 29, illustrates a preferred method of calibrating the automatic processing system using the computer control system. The calibration program begins, as the user places a balance on the working area. The balance, which can be any known device that accurately measured a quantity of liquid, interfaces with the computers using any well known computer interface, such as a serial interface.

A syringe is selected for calibration and an operator instructs the system to start the calibration program. A predetermined amount of fluid is delivered from the chosen syringe onto the balance and the results of the measurement are recorded by the program. This operation is repeated at least ten times. A report is generated which analyzes the results by standard statistical methods. If it appears that the syringe is not delivering an accurate amount of fluid, a troubleshooting guide is available for help in determining what steps to take to adjust the amount of fluid being delivered by the syringe. If another syringe is to be calibrated, the process is repeated, if not, the balance is removed and the system is ready for operation.

Production Program For A Single Rack

Figure 30:
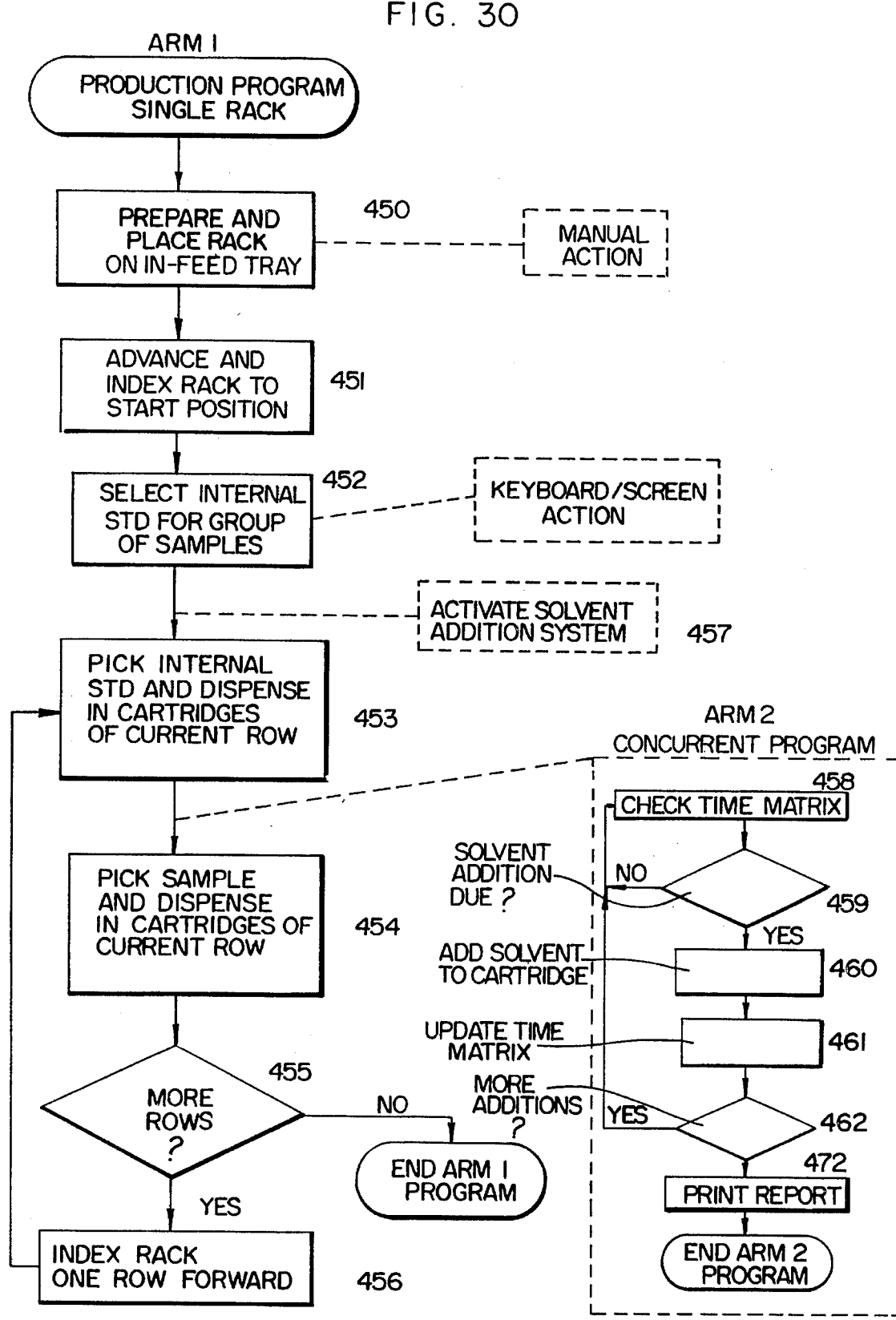
FIG. 30 is a flow chart of the production program for a single rack according to the present invention.

The production program for processing one rack is illustrated by the flow chart FIG. 30 illustrating the production program for a single rack which acts upon one rack only. The production program is divided into Arm 1, which describes the movement of the rack and the addition of internal standard and sample to the extraction cartridge, and Arm 2 which describes the operation of the solvent addition system.

Arm 1 of the production program begins at step 450 wherein a rack 72, is loaded by an operator with extraction cartridges 12 and a corresponding number of sample tubes 115 and collection tubes 110, is placed on either the input extension unit 680 or directly on the main processing platform 50.

At step 451, the rack is advanced to the start position so that the first row of cartridges, samples and extraction tubes is accessible to the robotic sampling system so that the addition of internal standard and samples can begin. This occurs in the following manner. First, if the input extension unit is used, the proximity sensor 217 in the input extension unit 680 sends a signal to the computer which signals the motor 682 to drive the conveyor 681 to move the rack 72 onto the working surface 51 of the main processing platform 50. When a proximity sensor 217 in the main processing platform 50 detects the presence of a rack 72, the motor 682 driving the rack 72 from the input extension unit 680 stops. The proximity sensor 217 sends a signal to the computer which signals the motor 200 to move the walking beam 250 a sufficient number of revolutions so that the first row of cartridges 12, collection tubes 110 and sample tubes 115 is positioned underneath the robotic sampling system 40.

The next step in the production program 452 is the selection of an internal standard for the samples that are in the rack. This is done by the operator who inputs the instructions as to which internal standard to use. Also, the operator inputs which solvent to deliver by the solvent addition system, which is activated automatically by the program.

The addition of internal standard and sample to the extraction cartridge begins at step 453 with the addition of an internal standard to each cartridge in the first row. The first pipette 48 moves to an internal standard tube 63 which holds the internal standard, whose type has been inputted into the computer, and picks up a predetermined volume of internal standard. The first pipette 48 then moves above the first row of cartridges 12 and deposits the internal standard in each cartridge. The first pipette 48 then moves to the wash station 62 where it is thoroughly washed.

The next step in the production program 454 is the pickup of the sample from a sample tube and the dispensing of the sample into the cartridge. This is done by the first pipette 48 which moves to the first sample tube in the first row where it picks up the sample, moves to the first cartridge in the row and deposits the sample. The process of picking up a sample and depositing it in a cartridge is repeated along the first row until each of the samples is deposited in their corresponding cartridges. The first pipette 48 moves to the wash station 62 and is washed between each sample addition.

After the first row is complete, the program, at step 455 determines if there are more rows of samples to be deposited into cartridges. If the answer is yes, as shown in the flow chart at step 456, a signal is sent to the computer which signals the motor 200 to move one revolution and thereby index the rack forward one position so that the next row is under the robotic sampling system 40. The next row is processed in the same manner and Arm 1 of the production program continues until all of the rows have been completed. When there are no more rows that need to have internal standard and samples added to the extraction cartridges, Arm 1 of the production program is complete.

Operating concurrently with Arm 1 is the solvent addition system 457. This system tracks the time that has elapsed from when the sample is placed in the cartridge as well as the time between each addition of solvent. As was described above, both of these times are important to obtaining a complete extraction of a particular substance from the sample. Unlike the addition of the internal standard and sample, the addition of solvent is not completed on a row by row basis. As will be described below, the software includes a time matrix that tracks the time each sample is added to the cartridge and the time between each solvent addition. Accordingly, if a sample in the first row needs its fourth solvent addition, and the next sample that needs a solvent addition is in the third row, the computer is capable of tracking both of these times and instructing the solvent system to add solvent accordingly.

For example, as the first sample is added to the cartridge, the time matrix in Arm 2 is checked at step 458 to determine when a solvent addition is due in the cartridge which is illustrated at step 459. If the answer is yes, step 460 adds solvent to the cartridge in the following manner. A signal is sent from the computer which activates second pipette 45, to add a predetermined amount of solvent to the cartridge. The time matrix is updated at step 461 to start counting the next time interval for the next addition of solvent. At step 462, the computer determines if more solvent additions are needed, if yes, Arm 2 continues by updating the time matrix and determining the next sample that needs a solvent addition. If no more solvent additions are required, a report is printed at step 472 and the program is completed, ending the production run.

As noted above, the processing of each row, including placing the samples into the cartridges by first pipette 48 and addition of the solvent by second pipette 45 continues simultaneously until the entire rack 72 is processed with the addition of sample, internal standard and solvent. When the processing of the rack is completed, the program instructs the system to remove the rack from the main processing platform, by sending a signal to the motor controlling the conveyor on the output extension unit 84 to move the rack off the main processing unit 50 and onto the output extension unit 84. An operator then removes the rack for further processing of the collection tubes, as well as recycling of the cartridges.

Production Program for Multiple Racks

Figure 31:
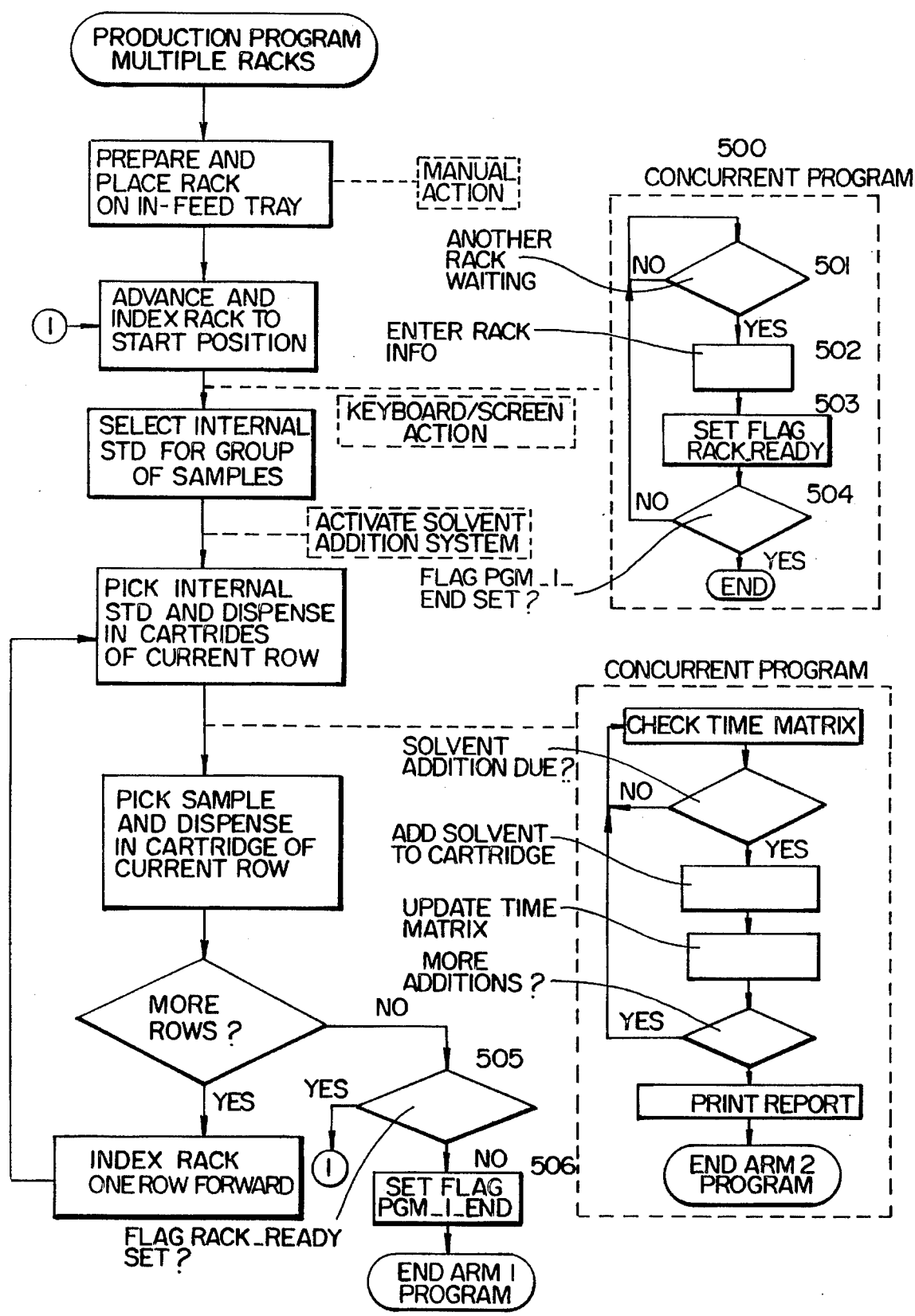
FIG. 31 is a flow chart of the production program for multiple racks according to the present invention.

FIG. 31 is a flow chart of the production program for multiple racks which acts upon consecutive racks without process interruption. The production program for multiple racks is substantially similar to the production program for a single rack with the addition of a concurrent program 500 that determines if another rack is ready for processing. At step 501, a proximity sensor sends a signal to the computer if another rack has been placed on the input extension unit. If the answer is yes, the information about this rack is manually entered into the computer at step 502, and a flag, Rack-Ready, is set at step 503 indicating that another rack is ready to be processed. At step 504 the computer asks if the flag PGM_1_END, which will be described below, has been set, if the answer is yes, than no additional rack is ready for processing and the program ends.

As noted above, the concurrent program sets a flag if another rack is ready to be processed. At step 505, the computer asks if the flag Rack Ready has been set. If the answer is yes, then the processing of the next rack starts by advancing the rack to the start position when the internal standard and sample addition for the last row of the rack has been completed. If the answer is no, the computer, at step 506 sets the flag PGM_1_END, which is used during the concurrent program, as described above, and Arm 1 is completed.

So as not to be unduly duplicative, the remaining steps of the production development program for multiple racks will not be described because they are substantially identical to the steps of the production program for a single rack which are described above.

Method Development Program

Figure 32:
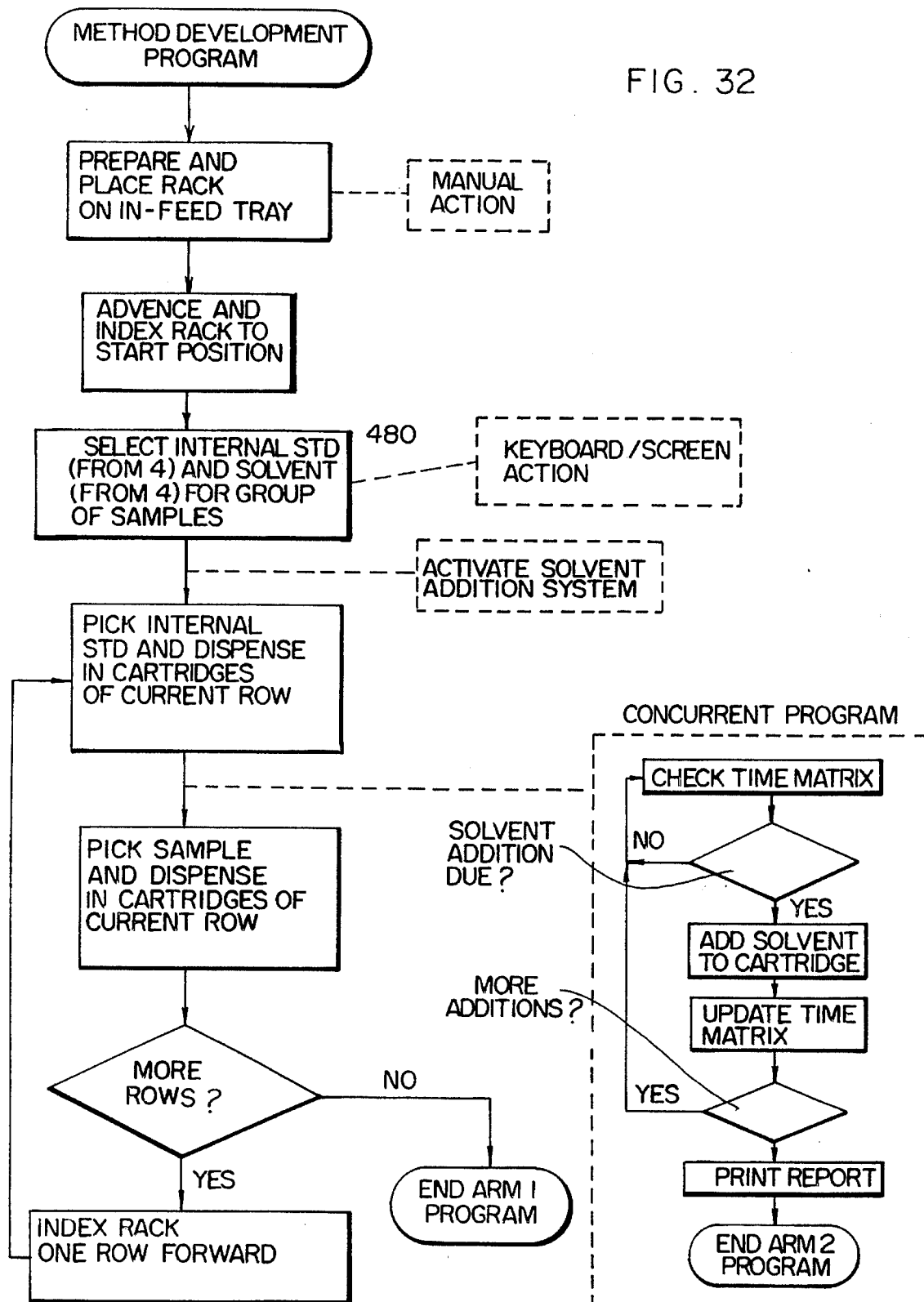
FIG. 32 is a flow chart of the method development program according to the present invention.

FIG. 32 is a flow chart of the method development program. The method development program allows a carefully designed, complex experiment to be carried out automatically. Normally, an analyst must determine the best cartridge, solvent and internal standard to be used to extract a particular drug, through a painstaking series of trial and error experiments. The method development program can complete this task in a matter of hours.

As is shown in FIG. 32, the method development program is substantially similar to the production program for a single rack illustrated in FIG. 30. The difference between the method development program and the production program for a single rack is step 480. At this step, instead of imputing an internal standard and solvent that are known to be capable of extracting the drug, the operator inputs a series of combinations of internal standards and solvents.

For example, if the apparatus is equipped to deliver four internal standard and four solvents, it is possible to test sixteen different combinations of solvent and internal standard on the same drug to determine which combination produces a complete, clean extraction for a particular cartridge. Furthermore, the same combination of solvents and internal standards can be applied to a number of different cartridges to determine which cartridge is best suited for extracting a particular drug.

So as not to be unduly duplicative, the remaining steps of the method development program will not be described because they are substantially identical to the steps of the production program which are described above.

Any manual input of data to the automatic processing system can also be accomplished automatically by using well known automatic data entry systems. For example, the data can be inputted using a bar code indicating the information cooperating with any automated bar code reader.

As has been described above, the present invention includes among other features, an extraction cartridge, a method of extracting substances from fluids, and an automatic processing system, which includes an apparatus for automatically performing an extraction process and a computer system for controlling the automatic processing.

The processing system according to the present invention has the following advantages. The locking pins ensure absolute positive and accurate registration of the sample rack. The finite movements of the beam and rack allow the computer to calculate the exact position of each sample tube and provide appropriate instructions to the robotic arms. Careful design of the cam controlling the positioning of the rack can minimize the possibility of spilling sample or extract. This is done by graded acceleration at the beginning of a rack movement and setting it gently back down despite the considerable weight of a fully loaded rack.

Further advantages of the processing system according to the present invention are that the apparatus is simple and reliable. The walking beam allows precise, reproducible positioning of the sample using locating pins, and ready identification of the exact position of a sample after any number of rack movements. The system is fully automated with complete synchronization between rack movement, position of the two robotic arms and the liquid handling system. The processing system allows for the extraction of over 140 samples per hour.

Still further advantages of the processing system according to the present invention include the ability to produce extracts biological fluids that are clean enough for direct injection in HPLCs, GCs and for some drugs directly into mass spectrometers without prior chromatography. The processing system is a single dedicated system with high throughput. The system provides a range of preprogrammed methods adequate for the extraction of most drugs and the ability for the user to rapidly develop methods for other drugs. Once actuated the system is fully automatic and operates unattended. Additional racks of samples, which can contain different drugs, are continuously processed. The system included built in detection of errors and problems, a calibration routine and a self-diagnostic routine. All working parts are readily accessible for easy service and the apparatus is designed to be resistant to solvent spills.

The automated extraction process according to the present invention has numerous advantages when compared to solid phase extraction or liquid-liquid extraction. Solid phase extraction may include conditioning of the extraction cartridge, manual measurement and transfer of sample, internal standard, buffer and solvent, an organic wash step and vacuum or pressurization. Liquid-liquid also may include manual measurement and transfer of sample, internal standard, buffer and solvent and an organic wash step as well as shaking and centrifugation of the sample. In contrast, the automated extraction process according to the present invention does not require a conditioning step, provides automatic sample, internal standard and solvent transfer, does not need measurement of buffer, and does not need vacuum, pressurization, shaking, or centrifugation. The extracts produced by the present invention are cleaner with a higher percent of drug recovery than extracts produced by liquid-liquid or solid phase extraction.

While the invention has been described with reference to several exemplary embodiments, it is understood that the words which have been used herein are words of description and illustration, rather than words of limitations. Changes can be made, without departing from the scope and spirit of the invention in its aspects. The invention extends to all functionally equivalent structures, methods and uses, such as are within the scope of the appended claims.

What is claimed is:

1. A method for making an extraction cartridge comprising:

heating an inert support at a temperature of about 500° C. for about 3 hours;

mixing the heated inert support with a buffer;

heating diatomaceous earth at a temperature of about 500° C. for about 3 hours;

heating an adsorbent at a temperature of about 500° C. for about 3 hours;

positioning a first filter at the bottom of a cartridge;

adding the heated adsorbent to the cartridge;

adding the heated diatomaceous earth to the cartridge;

adding the mixture of heated support and buffer to the cartridge; and positioning a second filter in the cartridge.

* * * * *

UNITED STATES PATENT AND TRADEMARK OFFICE
CERTIFICATE OF CORRECTION

PATENT NO. : 5,603,160
DATED : February 18, 1997
INVENTOR(S) : D. LESSARD et al.

It is certified that error appears in the above-identified patent and that said Letters Patent is hereby corrected as shown below:

On the cover, in section [56], "References Cited", "U.S. PATENT DOCUMENTS", insert --- 3,674,722  7/1972  Rainer et al.---.

On the cover, in section [56], "References Cited", "U.S. PATENT DOCUMENTS", insert --- 3,796,657  3/1974  Pretorius et al.---.

On the cover, in section [56], "References Cited", "U.S. PATENT DOCUMENTS", insert --- 3,859,209  1/1975  Jahnsen et al.---.

On the cover, in section [56], "References Cited", "U.S. PATENT DOCUMENTS", insert --- 4,142,855  3/1979  Acuff---.

On the cover, in section [56], "References Cited", "U.S. PATENT DOCUMENTS", insert --- 4,301,139  11/1981  Feingers et al.---.

On the cover, in section [56], "References Cited", "U.S. PATENT DOCUMENTS", insert --- 4,309,286  1/1982  Lenihan Jr. et al.---.

On the cover, in section [56], "References Cited", "U.S. PATENT DOCUMENTS", insert --- 4,832,916  5/1989  Gilak---.

On the cover, in section [56], "References Cited", "U.S. PATENT DOCUMENTS", insert --- 4,871,675  10/1989  Coupek et al.---.

On the cover, in section [56], "References Cited", "U.S. PATENT DOCUMENTS", insert --- 4,990,458  2/1991  Rosenfeld---.

UNITED STATES PATENT AND TRADEMARK OFFICE
CERTIFICATE OF CORRECTION

PATENT NO. : 5,603,160

DATED : February 18, 1997

INVENTOR(S) : D. LESSARD et al.

Page 2 of 5

It is certified that error appears in the above-identified patent and that said Letters Patent is hereby corrected as shown below:

On the cover, in section [56], "References Cited", "U.S. PATENT DOCUMENTS", insert --- 5,057,437   10/1991   Binder---.

On the cover, in section [56], "References Cited", "U.S. PATENT DOCUMENTS", insert --- 5,071,769   12/1991   Kundu et al.---.

On the cover, in section [56], "References Cited", "U.S. PATENT DOCUMENTS", insert --- 5,085,781   2/1992   Tsuru et al.---.

On the cover, in section [56], "References Cited", "U.S. PATENT DOCUMENTS", insert --- 5,149,425   9/1992   Mazio---.

On the cover, in section [56], "References Cited", "U.S. PATENT DOCUMENTS", insert --- 5,178,832   11/1993   Phillips et al.---.

On the cover, in section [56], "References Cited", "U.S. PATENT DOCUMENTS", insert --- 5,238,556   8/1993   Shirkhan---.

On the cover, in section [56], "References Cited", "U.S. PATENT DOCUMENTS", insert --- 5,266,193   11/1993   Kimura et al.---.

On the cover, in section [56], "References Cited", "FOREIGN PATENT DOCUMENTS", insert --- 969482   6/1975   Canada---.

On the cover, in section [56], "References Cited", "FOREIGN PATENT DOCUMENTS", insert --- 2034946   7/1991   Canada---.

UNITED STATES PATENT AND TRADEMARK OFFICE
CERTIFICATE OF CORRECTION

PATENT NO. : 5,603,160
DATED : February 18, 1997
INVENTOR(S) : D. LESSARD et al.

It is certified that error appears in the above-identified patent and that said Letters Patent is hereby corrected as shown below:

On the cover, in section [56], "References Cited", "FOREIGN PATENT DOCUMENTS", insert ---1179277   12/1994   Canada---.

On the cover, in section [56], "References Cited", "OTHER PUBLICATIONS", insert ---Cavro Brochure for the Cavro SB 1200 Modular Digital Pump, March 1990---.

On the cover, in section [56], "References Cited", "OTHER PUBLICATIONS", insert ---Cavro Brochure for RSP 9000 Robotic Sample Processor, October 1993---.

On the cover, in section [56], "References Cited", "OTHER PUBLICATIONS", insert ---Cavro Brochure for XL 3000 Series Multi-Channel Pumps, November 1992---.

On the cover, in section [56], "References Cited", "OTHER PUBLICATIONS", insert ---Hamilton Brochure for Hamilton Microlab SPE High Performance Solid Phase Extraction, September 1991---.

On the cover, in section [56], "References Cited", "OTHER PUBLICATIONS", insert ---Packard Brochure for MultiPROBE Automated Multichannel Liquid Handling Systems, August 1992---.

On the cover, in section [56], "References Cited", "OTHER PUBLICATIONS", insert ---Zymark Brochure for BenchMate II Workstations, December 1992---.

UNITED STATES PATENT AND TRADEMARK OFFICE
CERTIFICATE OF CORRECTION

PATENT NO. : 5,603,160

DATED : February 18, 1997

INVENTOR(S) : D. LESSARD et al.

Page 4 of 5

It is certified that error appears in the above-identified patent and that said Letters Patent is hereby corrected as shown below:

On the cover, in section [56], "References Cited", "OTHER PUBLICATIONS", insert ---Gilson Brochure for Gilson ASPEC XL Solid Phase Extraction System, March 1993---.

On the cover, in section [56], "References Cited", "OTHER PUBLICATIONS", insert ---Hewlett Packard Brochure for HP 7686 Prepstation System, October 1992---.

On the cover, in section [56], "References Cited", "OTHER PUBLICATIONS", insert ---Tecan Brochure for Robotic Sample Processor 5000, September 1991---.

On the cover, in section [56], "References Cited", "OTHER PUBLICATIONS", insert ---Tecan Brochure for Robotic Sample Processor 8000, September 1991---.

On the cover, in section [56], "References Cited", "OTHER PUBLICATIONS", insert ---Merck Brochure for Extrelut Liquid-Liquid Extraction In Its Most Effective Form, November 1991---.

On the cover, in section [56], "References Cited", "OTHER PUBLICATIONS", insert ---BDH Brochure for Chromatography Products From BDH, October 1993---.

UNITED STATES PATENT AND TRADEMARK OFFICE
CERTIFICATE OF CORRECTION

PATENT NO.   : 5,603,160
DATED        : February 18, 1997
INVENTOR(S)  : D. LESSARD et al.

It is certified that error appears in the above-identified patent and that said Letters Patent is hereby corrected as shown below:

On the cover, in section [56], "References Cited", "OTHER PUBLICATIONS", insert ---Varian Analytical Supplies Catalog, 1993, The Competitive Edge, pages 66 and 67---.

Signed and Sealed this

Twenty-seventh Day of October, 1998

Attest:

BRUCE LEHMAN

*Attesting Officer*          *Commissioner of Patents and Trademarks*